(12) United States Patent
Berreau et al.

(10) Patent No.: US 9,840,488 B2
(45) Date of Patent: Dec. 12, 2017

(54) CARBON MONOXIDE RELEASING MOLECULES AND ASSOCIATED METHODS

(71) Applicants: Lisa M Berreau, Logan, UT (US); Stacey N. Anderson, Logan, UT (US)

(72) Inventors: Lisa M Berreau, Logan, UT (US); Stacey N. Anderson, Logan, UT (US)

(73) Assignee: Utah State University, Logan, UT (US)

( * ) Notice: Subject to any disclaimer, the term of this patent is extended or adjusted under 35 U.S.C. 154(b) by 0 days.

(21) Appl. No.: 15/007,033

(22) Filed: Jan. 26, 2016

(65) Prior Publication Data

US 2016/0214955 A1     Jul. 28, 2016

Related U.S. Application Data

(60) Provisional application No. 62/107,967, filed on Jan. 26, 2015.

(51) Int. Cl.
| | |
|---|---|
| *C07D 311/92* | (2006.01) |
| *C07D 409/10* | (2006.01) |
| *C07F 9/655* | (2006.01) |

(52) U.S. Cl.
CPC .......... *C07D 311/92* (2013.01); *C07D 409/10* (2013.01); *C07F 9/65522* (2013.01)

(58) Field of Classification Search
CPC .................................................. C07D 311/92
See application file for complete search history.

(56) References Cited

FOREIGN PATENT DOCUMENTS

| | | |
|---|---|---|
| JP | 2014141465 A | 8/2014 |
| JP | 2016008179 A | 1/2016 |

OTHER PUBLICATIONS

IUPAC Gold Book. © 2016. Available at: < http://goldbook.iupac.org/A00224.html >.*
IUPAC Gold Book. © 2016. Available at: < http://goldbook.iupac.org/A00236.html>.*
Bilokin, M.D., et al. "3-Hydroxybenzo[g]quinolones: dyes with red-shifted absorption and highly resolved dual emission." Tetrahedron Letters. (2009), vol. 50, pp. 4714-4719.*
Mann et al., Carbon Monoxide: An Essential Signalling Molecule, 32 Topics in Organolmetallic Chemistry 247-285 (2010).
Schatzschneider et al., Novel lead structures and activation mechanisms for CO-releasing molecules (CORMs), 172 British Journal of Pharmacology 1638-1650 (2015).
Gonzales et al., Photoactive metal carbonyl complexes as potential agents for targeted CO delivery, 133 Journal of Inorganic Biochemistry 127-135 (2014).
Chakraborty et al., Design Strategies to Improve the Sensitivity of Photoactive Metal Carbonyl Complexes (photoCORMs) to Visible Light and Their Potential as CO-Donors to Biological Targets, 47:8 Accounts of Chemical Research 2603-2611 (2014).
Zobi et al., CO and CO-releasing molecules in medicinal chemistry, 5:2 Future Med. Chem. 175-188 (2013).
Antony et al., Flurescein Analogue Xanthene-9-Carboxylic Acid: A Transition-Metal-Free CO Releasing Molecule Activated by Green Light, 15:17 Organic Letters 4552-4555 (2013).
Peng et al., Visible-light activatable organic CO-releasing molecules (PhotoCORMs) that simultaneously generate fluorophores, 11:39 Organic & Biomolecular Chemistry 6671-6674 (2013).
Wang et al., A click-and-release apprach to CO prodrugs, 50 ChemComm 15890-15893 (2014).
Palao et al., Transition-Metal-Free CO-Releasing BODIPY Derivatives Activatable by Visible to NIR Light as Promising Bioactive Molecules, 138 Journal of the American Chemical Society 126-133 (2016).
Zenkevich et al., Identification of the Products of Oxidation of Quercetin by Air Oxygen at Ambient Temperature, 12 Molecules 654-672 (2007).
Shynkar et al., Fluorescent Biomembrane Probe for Ratiometric Detection of Apoptosis, 129 Journal of the American Chemical Society 2187-2193 (2007).
Duportail et al., Neutral fluorescence probe with strong ratiometric response to surface charge of phospholipid membranes, 508 FEBS Letters 196-200 (2001).
Bondar et al., Flavonols—new fluorescent membrane probes for studying the interdigitation of lipid bilayers, 1369 Biochimica et Biophysica Acta 119-130 (1998).
Sytnik et al., Interplay between excited-state intramolecular proton transfer and charge transfer in flavonols and their use as protein-binding-site fluorescence probes, 91 Proc. Natl. Acad. Sci. 11968-11972 (1994).
Macanita et al., Photochemistry of Flavothione and Hydroxyflavothiones: Mechanisms and Kinetics, 77:1 Photochemistry and Photobiology 22-29 (2002).
Borges et al., Photobiological Properties of Hydroxy-substituted Flavothiones, 75:2 Photochemistry and Photobiology 97-106 (2002).
Elisei et al., Photophysical Properties of Hydroxy-Substituted Flavothiones, 104 J. Phys. Chem. 6095-6102 (2000).
D'Andrea, Quercetin: A flavonol with multifaceted therapeutic applications?, 106 Fitoterapia 256-271 (2015).

(Continued)

*Primary Examiner* — Noble Jarrell
*Assistant Examiner* — John S Kenyon

(57) ABSTRACT

The present disclosure relates to carbon monoxide releasing molecules ("CORMs"), and methods of synthesizing and applying the molecules. More specifically, this disclosure relates to structurally tunable CORMS, compounds containing CORMS (and salts thereof). An exemplary compound includes:

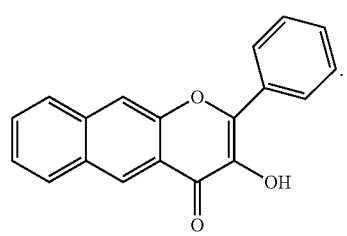

14 Claims, 22 Drawing Sheets

(56) References Cited

OTHER PUBLICATIONS

Perez et al., Evaluating Prodrug Strategies for Esterase-Triggered Release of Alcohols, 8:10 ChemMedChem 1662-1667 (2013).
Schallner et al., Friend or foe? Carbon monoxide and the mitochondria, 6 Frontiers in Physiology 1-4 (2015).
Almeida et al., Carbon monoxide and mitochondria—modulation of cell metabolism, redox response and cell death, 6 Frontiers in Physiology 1-6 (2015).
Bilokin et al., 3-Hydroxybenzo[g]quinolones: dyes with red-shifted absorption and highly resolved dual emission, 50 Tetrahedron Letters 4714-4719 (2009).
International Search Report and Written Opinion for PCT/US16/14983, filed Jan. 26, 2016, dated Mar. 30, 2016.

* cited by examiner

| Measured Mass | 360.1594 | | | |
|---|---|---|---|---|
| Element | Low Limit | High Limit | | |
| C | 17 | 27 | | |
| H | 15 | 35 | | |
| N | 0 | 2 | | |
| O | 2 | 5 | | |
| Formula | Calculated Mass | mDaError | ppmError | RDB |
| C23 H22 N O3 | 360.1594 | 0.0 | -0.1 | 13.5 |

| Measured Mass | 637.0757 | |
|---|---|---|
| Element | Low Limit | High Limit |
| C | 30 | 40 |
| H | 15 | 35 |
| O | 4 | 8 |
| S | 0 | 2 |
| Na | 0 | 1 |

| Formula | Calculated Mass | mDaError | ppmError | RDB |
|---|---|---|---|---|
| C36 H22 O6 Na S2 | 637.0750 | 0.7 | 1.1 | 25.5 |
| C38 H21 O6 S2 | 637.0774 | -1.7 | -2.7 | 26.5 |

CARBON MONOXIDE RELEASING MOLECULES AND ASSOCIATED METHODS

RELATED APPLICATIONS

This application claims priority to U.S. Provisional Application No. 62/107,967, flied Jan. 26, 2015, the entirety of which is hereby incorporated by reference. This application is related to S. A. Anderson, J. M. Richards, H. J. Esquer, A. D. Benninghoff, A. M. Arif, L. M. Berreau, A Structurally-Tunable 3-Hydroxyflavone Motif for Visible Light-Induced Carbon Monoxide-Releasing Molecules (CORMs), 4 ChemistryOpen 590-594 (2015), the entirety of which is incorporated by reference in its entirety.

GOVERNMENT SPONSORED RESEARCH

This invention was made with government support under Contract No. CHE-1301092 awarded by the National Science Foundation. The government has certain rights in the invention.

TECHNICAL FIELD

The present disclosure relates to carbon monoxide releasing molecules ("CORMs"), and methods of synthesizing and applying the molecules. More specifically, this disclosure relates to structurally tunable CORMs.

SUMMARY

The present disclosure provides structurally tunable CORMs, including, for example, the CORMs set forth below in Formula I.

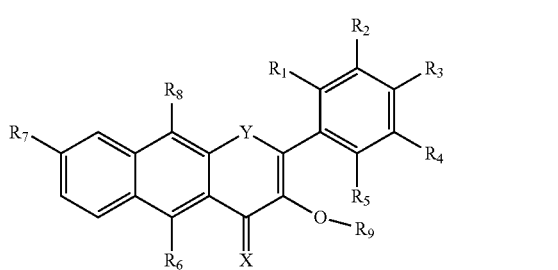

Formula I

Where:
Y=O, NH, or S;
X=O or S;
$R_1$, $R_2$, $R_4$, $R_5$, $R_6$, $R_7$, $R_8$ may each be selected from the group consisting of —H; —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —C$_{5-n}$ aryl optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; $C_{1-12}$ alkyl straight or branched optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —P(aryl)$_3$; P(alkyl)$_3$; PO$_3^{2-}$; HPO$_3^-$; —C$_{1-12}$ alkenyl optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —P(aryl)$_3$; P(alkyl)$_3$; PO$_3^{2-}$; HPO$_3^-$; $C_{1-12}$ alkynyl optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —P(aryl)$_3$; P(alkyl)$_3$; PO$_3^{2-}$; HPO$_3^-$; $C_{1-12}$ alkyl —$C_{5-n}$ aryl optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —P(aryl)$_3$; P(alkyl)$_3$; PO$_3^{2-}$; HPO$_3^-$; $C_{1-12}$ alkenyl-$C_{5-n}$ aryl optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —P(aryl)$_3$; P(alkyl)$_3$; PO$_3^{2-}$; HPO$_3^-$; amino acids; aminoglycosides; carbohydrates; heterocycles containing O, N, or S optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; P(alkyl)$_3$; PO$_3^2$; HPO$_3$;

where R' is aryl 5-n C atoms, alkyl, alkenyl, or alkynyl 1-12 C atoms straight or branched;

$R_3$=—H; —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^2$; HPO$_3^-$; —C$_{5-n}$ aryl optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$; $C_{1-12}$ alkyl straight or branched optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$; alkenyl optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$; $C_{1-12}$ alkynyl optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3$; $C_{1-12}$ alkyl-$C_{5-n}$ aryl optionally substituted with —COOH;

—CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^{3-}$; C$_{1-12}$ alkenyl-C$_{5-n}$ aryl optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$; amino acids; aminoglycosides; carbohydrates; heterocycles containing O, N, or S optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$;

where R" is aryl 5-n C atoms, alkyl, alkenyl, or alkynyl 1-12 C atoms straight or branched; and where n may be from 1 to 15, such as 1, 2, 3, 4, 5, 6, 7, 8, 9, 10, 11, 12, 13, 14, or 15;

R$_9$=—COR"" where R"" is aryl 5-n C atoms, alkyl, alkenyl, or alkynyl 1-12 C atoms straight or branched;

BRIEF DESCRIPTION OF THE DRAWINGS

FIG. 9(a) illustrates $^1$H NMR spectrum an exemplary compound (compound 5) in CD$_3$CN at ambient temperature and FIG. 9(b) illustrates $^1$H NMR spectrum obtained after irradiation of the an exemplary compound (compound 5) at 419 nm for 24 h. The results indicate clean conversion to another exemplary compound (compound 6).

FIG. 10(a) illustrates $^1$H NMR spectrum an exemplary compound (compound 5) in CD$_3$OD at ambient temperature and FIG. 10(b) illustrates $^1$H NMR spectrum obtained after irradiation of the exemplary compound (compound 5) at 419 nm for 24 h. The results indicate conversion to another exemplary compound (compound 6).

DETAILED DESCRIPTION

Figure 1:
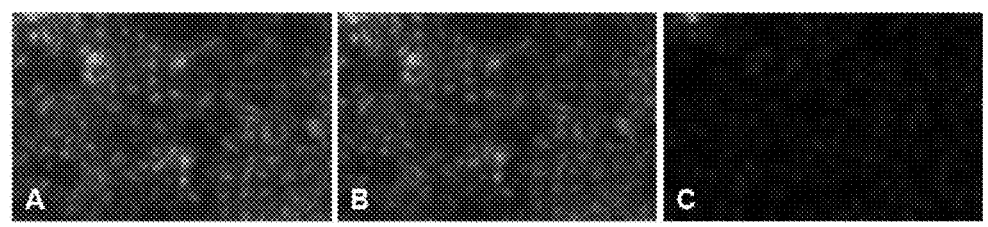
FIG. 1 illustrates fluorescence microscopy of human lung cancer (A549) cells treated with an exemplary compound (compound 5) for 1 hr, then excited with visible light for a) 30 sec, b) 3 min, and c) 10 min. Pictures represent overlay images for fluorescence detection of 5 (green) and the nuclear Hoechst stain (blue). Loss of fluorescence with increasing length of exposure to visible light indicated photoinduced CO release from compound 5. See FIG. 13 for separate images of each detection channel and the complete field of view observed.

CORMs are of significant current interest as potential therapeutics.[1] The vast majority of CORMs developed to date are based on a metal-carbonyl unit as the CO-releasing moiety.[2] Many molecules of this type, including protein-bound derivatives of [RuCl(glycinato)(CO)$_3$ (CORM-3 below), release CO spontaneously through ligand exchange in an aqueous environment.[3] The lack of temporal control for CO-release in such systems has led to the development of metal carbonyl complexes that release CO only when triggered.[4,5] Examples of such complexes include photo-CORMs, which release CO from a metal carbonyl unit upon irradiation with UV or visible light.[4] Recent advances in the field of photoCORMs demonstrate that through modification of the supporting ligands in such complexes, CO release can be tuned to occur upon irradiation with low-energy red light.[4b,4c]

However, problems associated with metal-carbonyl based photoCORMs include the reversibility of the CO-release reaction, and the potential toxicity associated with the low-valent metal photo remnant that remains following CO release.[4c,5,6] To avoid this issue, a few molecules that release CO from other types of structural motifs have been evaluated.[7,8] These include αα-dialkylaldehydes, oxalates, silacarboxylates, and boroncarboxylates (e.g. Na$_2$[H$_3$BCO$_2$], CORM A-1, below), as well as four recently reported polycyclic organic compounds (1-4, below).

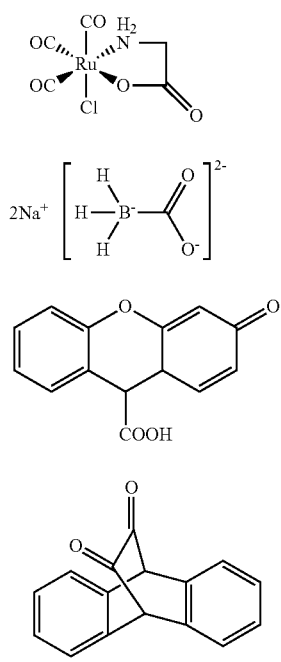

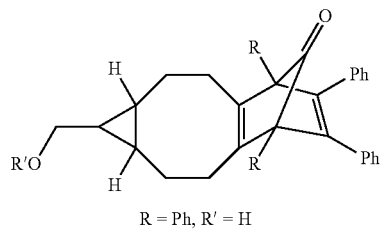

R = Ph, R' = H

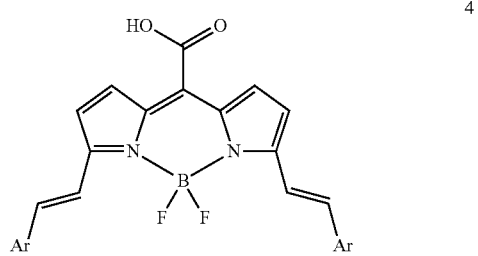

These molecules all have limitations. For example, the organic photoCORMs 1 and 2 are derived from relatively low-yield, multistep synthetic routes that have not been shown to be amenable to structural modification for the tuning of physical properties or biological targeting.

The Diels-Alder product 3 can be generated in good yield and subsequently undergoes CO release. However, this compound cannot be isolated and stored. It has also not been shown to form and undergo CO release within cells, likely due to the reactivity of one of the starting reagents (bicycle-[6.1.0]nonyne) to bioconjugate with proteins.[8]

The bodipy derivative 4 offers the possibility of using tissue-penetrating red light to induce CO release. However, the organic byproducts remaining following the CO-release reaction have not been identified.

Desirable features in next generation organic photo-CORMs would be: (1) a high-yield synthesis that enables the preparation of gram quantities of analytically pure compound; (2) solubility in water or aqueous DMSO; (3) thermal stability in aerobic, aqueous environments; (4) controllable, triggered CO release, preferably using an approach (e.g. using low-energy visible light) that does not have the potential to impart cellular damage; (5) low toxicity for the CORM and its post-CO-release byproducts; (6) ease of structural modification to modulate aqueous solubility, photochemical properties (e.g. light absorption properties), and biocompatibility, and (7) exhibits fluorescence so as to enable tracking of the localization of the molecule within cells.[9] In the results reported herein, we report a new type of biologically-inspired organic photoCORM that exhibits many of the desirable features noted above. This family of molecules is based on a 3-hydroxylflavone motif, which is found in molecules that are already known to exhibit several types of biological activity, including antioxidant, anti-inflammatory, and anti-cancer activity, as well as protection against cardiovascular disease.[10]

Naturally-occurring 3-hydroxyflavone derivatives, such as quercetin (Scheme 1(top)), are known to undergo enzyme-catalyzed oxidative degradation to produce CO.[11] However, in the absence of enzyme, quercetin undergoes a variety of oxidative reactions, including light induced reactions, some of which do not result in CO release.[12] It is known that 3-hydroxyflavone (3-HFlH) will undergo a photoinduced dioxygenation with release of one equivalent of CO either in the presence of photosensitizer-generated $^1O_2$, or via direct irradiation using UV light (Scheme 1 (bottom)).[13] These reactions are proposed to proceed from the normal and tautomeric excited state forms of 3-HlfH, respectively. It has also been reported that 3-HflH will undergo a photoinduced rearrangement resulting in CO release under anaerobic conditions.[14]

cumstances occurs, and to instances in which more than one of the subsequently described circumstances occurs.

The present disclosure covers methods, compositions, reagents, and kits for synthesizing structurally tunable CORMs. Exemplary CORMs includes those set forth below in Formula I.

Scheme 1.

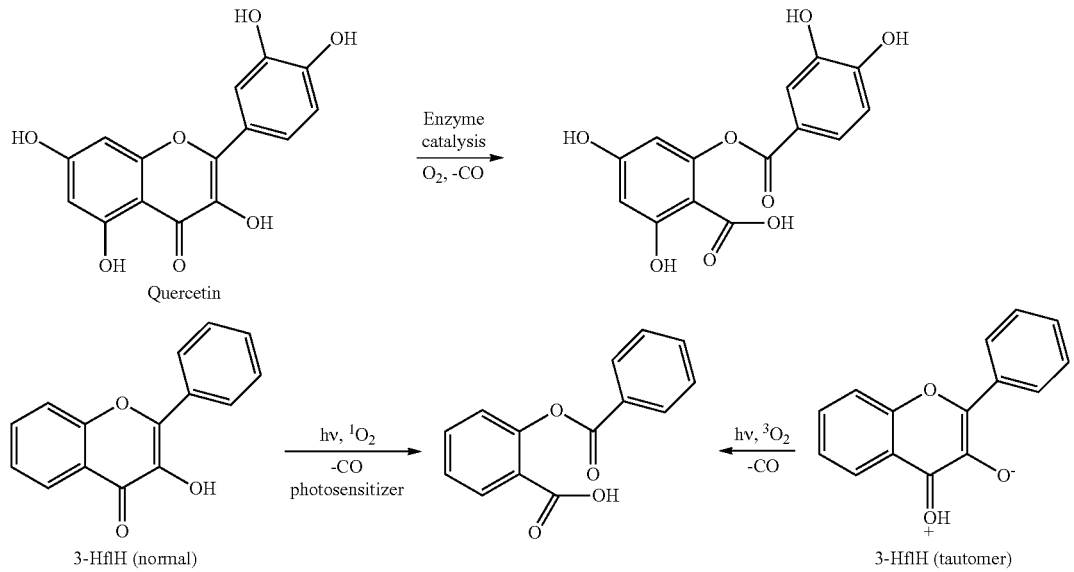

top) Enzyme-catalyzed CO release from quercetin. bottom) Reaction of 3-HflH with $^1O_2$ (generated via photosensitization); proposed reaction of the tautomeric form of 3-HflH with $O_2$ upon direct irradiation with UV light.

The present disclosure covers apparatuses and associated methods for synthesizing structurally tunable CORMs. In the following description, numerous specific details are provided for a thorough understanding of specific preferred embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of alternative embodiments. Thus, the following more detailed description of the embodiments of the present invention, as illustrated in some aspects in the drawings, is not intended to limit the scope of the invention, but is merely representative of the various embodiments of the invention.

In this specification and the claims that follow, singular forms such as "a," "an," and "the" include plural forms unless the content clearly dictates otherwise. All ranges disclosed herein include, unless specifically indicated, all endpoints and intermediate values. In addition, "optional" or "optionally" refer, for example, to instances in which subsequently described circumstance may or may not occur, and include instances in which the circumstance occurs and instances in which the circumstance does not occur. The terms "one or more" and "at least one" refer, for example, to instances in which one of the subsequently described cir-

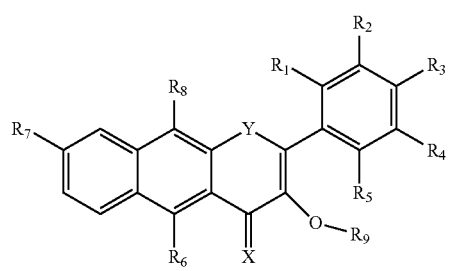

Formula I

Where:
Y=O, NH, or S;
X=O or S;
$R_1$, $R_2$, $R_4$, $R_5$, $R_6$, $R_7$, $R_8$ may be the same or different;
$R_1$, $R_2$, $R_4$, $R_5$, $R_6$, $R_7$, $R_8$ may each be selected from the group consisting of —H; —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —C$_{5\text{-}n}$ aryl optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —C$_{1\text{-}12}$ alkyl straight or branched optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'—SO$_3$R'; —OSO$_2$R'; —P(aryl)$_3$; P(alkyl)$_3$; PO$_3^{2-}$; HPO$_3^-$; —C$_{1-12}$ alkenyl optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —P(aryl)$_3$; P(alkyl)$_3$; PO$_3^{2-}$; HPO$_3^-$; C$_{1-12}$ alkynyl optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —P(aryl)$_3$; P(alkyl)$_3$; PO$_3^{2-}$; HPO$_3^-$; C$_{1-12}$ alkyl-C$_{5-n}$ aryl optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —P(aryl)$_3$; P(alkyl)$_3$; PO$_3^{2-}$; HPO$_3^-$; C$_{1-12}$ alkenyl-C$_{5-n}$ aryl optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —P(aryl)$_3$; P(alkyl)$_3$; PO$_3^{2-}$; HPO$_3^-$; amino acids; aminoglycosides; carbohydrates; heterocycles containing O, N, or S optionally substituted with —COOH; —CSOH; —COOR'; —CONH$_2$; —CONHR'; CON(R')$_2$; —COR'; —F; —Cl; —Br; —I; —CN; —NO$_2$; —OH; —OR'; —SH; —SR'; —O—CO—R'; —NH$_2$; —NHR'; —NR$_2$'; —NH(R')$_2$; —NH—CO—R'; —NR'—CO—R'; —SO$_3$R'; —OSO$_2$R'; —P(aryl)$_3$; P(alkyl)$_3$; PO$_3^2$; HPO$_3$;

where R' is aryl 5-n C atoms, alkyl, alkenyl, or alkynyl 1-12 C atoms straight or branched;

R$_3$=—H, —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$; —O$_{5-n}$ aryl optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$; C$_{1-12}$ alkyl straight or branched optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$; —C$_{1-12}$ alkenyl optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$; C$_{1-12}$ alkynyl optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$; C$_{1-12}$ alkyl-C$_{5-n}$ aryl optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$; C$_{1-12}$ alkenyl-C$_{5-n}$ aryl optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$; amino acids; aminoglycosides; carbohydrates; heterocycles containing O, N, or S optionally substituted with —COOH; —CSOH; —COOR"; —CONH$_2$; —CONHR"; CON(R")$_2$; —COR"; —F; —Cl; —Br; —I; —CN; —NO$_2$; —OH; —OR"; —SH; —SR"; —O—CO—R"; —NH$_2$; —NHR"; —NR$_2$'; —NH(R")$_2$; —NH—CO—R"; —NR"—CO—R"; —SO$_3$R"; —OSO$_2$R"; —P(aryl)$_3$; P(alkyl)$_3$; PO$_3^{2-}$; HPO$_3^-$;

where R" is aryl 5-n C atoms, alkyl, alkenyl, or alkynyl 1-12 C atoms straight or branched; and where n is _10_.

R$_9$=—COR"" where R"" is aryl 5-n C atoms, alkyl, alkenyl, or alkynyl 1-12 C atoms straight or branched;

In some embodiments, the CORMs may be selected from the following:

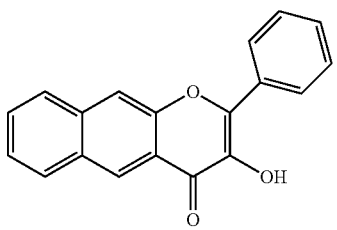

Formula II

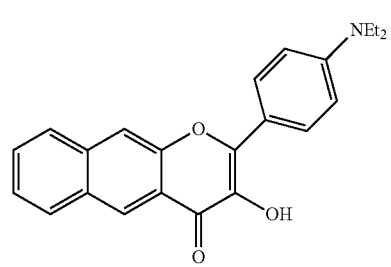

Formula III

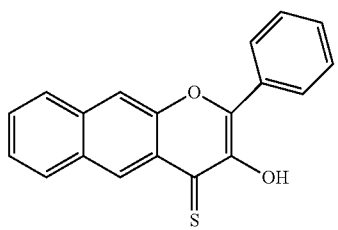

Formula IV

Formula V

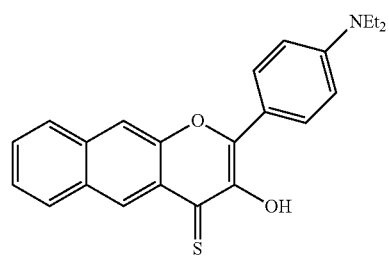

Formula VI

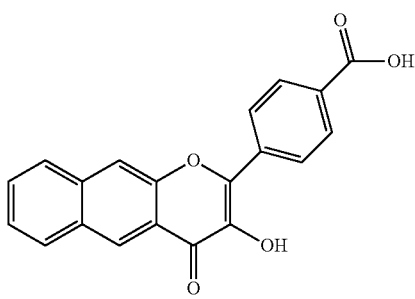

Formula VII

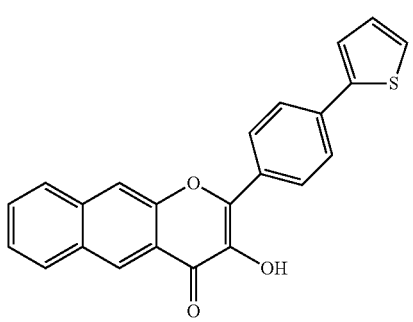

Formula VIII

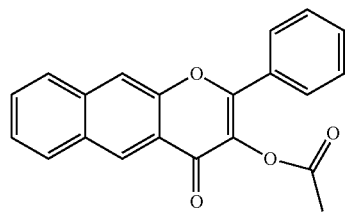

Formula IX

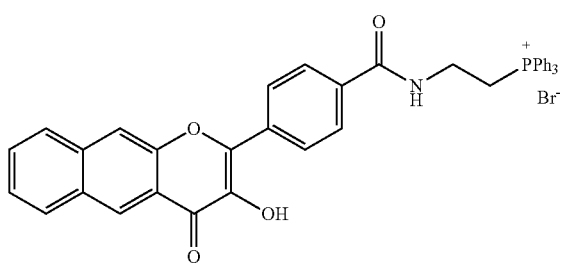

Formula X

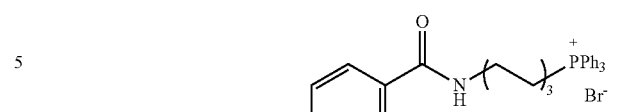

Formula XI

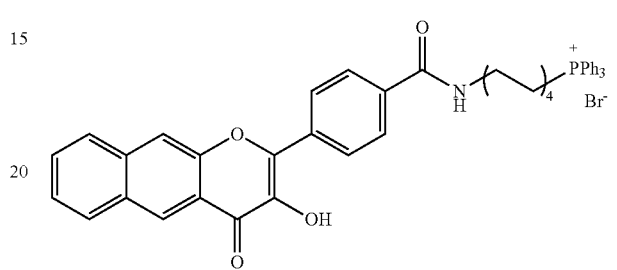

In embodiments, the compound, or salt thereof, may be combined with suitable additives. Suitable additives include pharmaceutically acceptable carrier compositions and/or compounds.

We have reexamined the photoinduced ($\lambda_{irr}$=300 nm) reaction of 3-HflH with $O_2$ and found that while a nearly quantitative amount of CO is generated (0.95 eq), multiple organic products are detected by GC-MS. These results suggested to us that 3-hydroxyflavone derivatives might be structurally tuned to undergo visible light-induced quantitative CO release.

With this strategy in mind, the new 3-hydroxyflavone 5 was designed and prepared in multi-gram quantity using the Alger-Flynn-Oyamada methodology[15] (below).

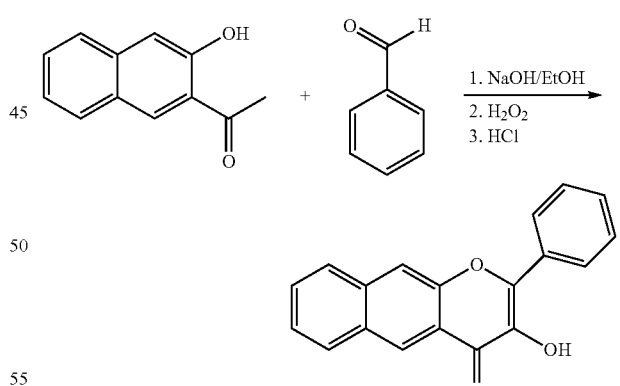

5, 62%

Figure 4:
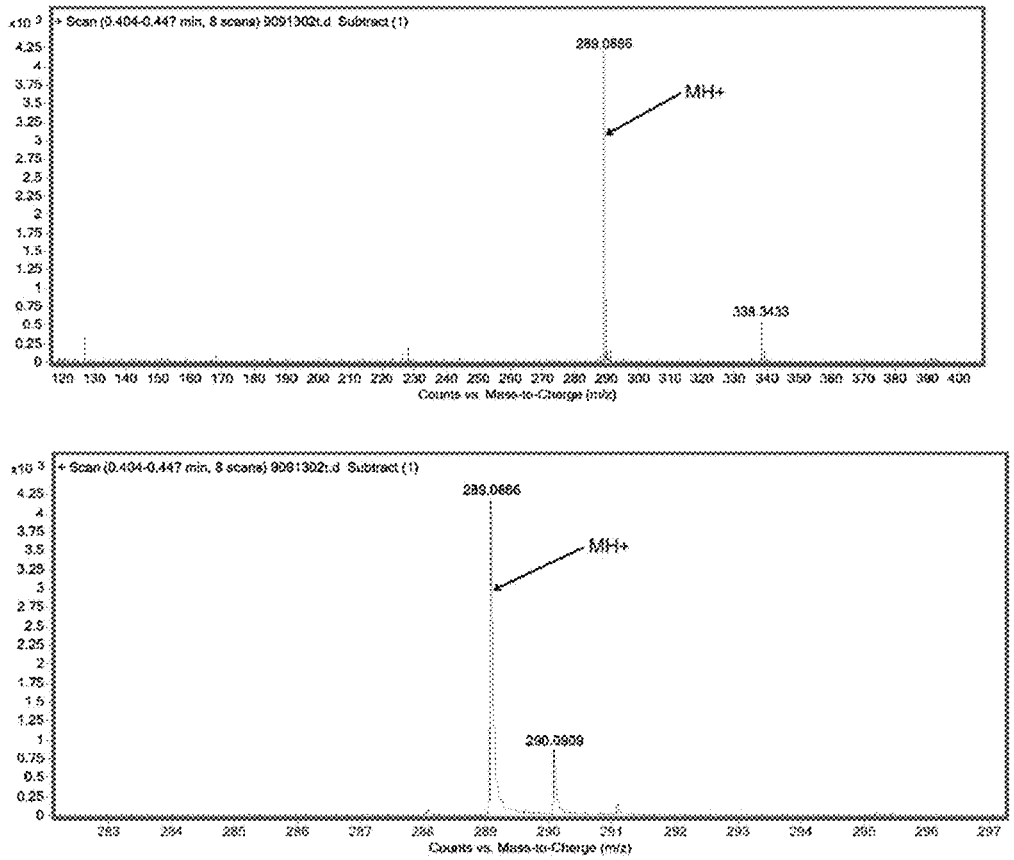
FIG. 4 illustrates ESI/APCI-MS of an exemplary compound (compound 5).

The compound precipitates from the final reaction mixture and requires only washing with ethanol and drying to be isolated in analytically pure form. X-ray quality crystals of 5 were obtained via slow evaporation of $CH_2Cl_2$ solution. Compound 5 was additionally characterized by elemental analysis, spectroscopic methods (FIGS. 3 and 5-7) and mass spectrometry (FIG. 4). It is readily soluble in organic solvents ($CH_3CN$, $CH_2Cl_2$, $CHCl_3$, DMSO) and is also soluble in aqueous DMSO (e.g. 1:1 $H_2O$:DMSO for spectroscopic measurements and 0.1% DMSO/RPMI cell culture media for biological experiments) at concentrations suitable for spectroscopic measurements and biological experiments.

Compound 5 crystallizes in the monoclinic space group C2/c.[16] The 3-hydroxy-4-pyrone units from two molecules form centrosymmetric hydrogen bonded dimers with two identical intermolecular O—H . . . O hydrogen bonds (O . . . O 2.69 Å; 145.3°). This is a common feature of the solid state structures of 3-hydroxyflavone derivatives.[17] The naphthyl-fused 3-hydroxy-4-pyrone ring structure is nearly planar, and the phenyl appendage twists only slightly out of this plane (dihedral angle 168.39°), This overall structure favors conjugation of the two electronic systems. Compound 5 has bond lengths and angles very similar to those of 3-hydroxyflavone (3-HflH).[17b]

Figure 5:
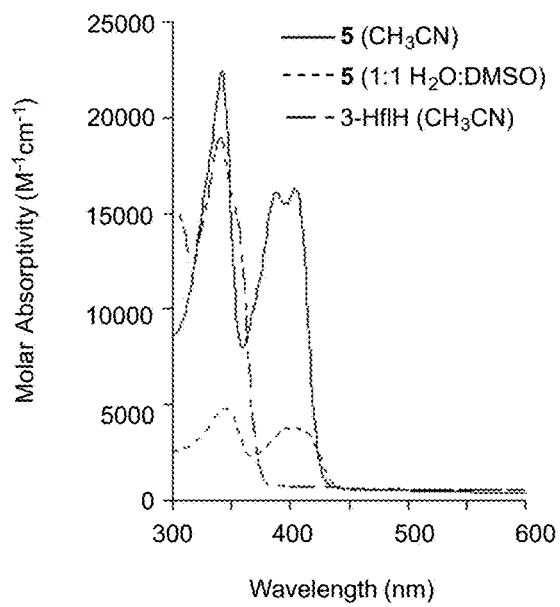
FIG. 5 illustrates absorption spectra of an exemplary compound (compound 5) in dry CH$_3$CN and 1:1 H$_2$O:DMSO, and 3-hydroxyflavone in CH$_3$CN.
Figure 6:
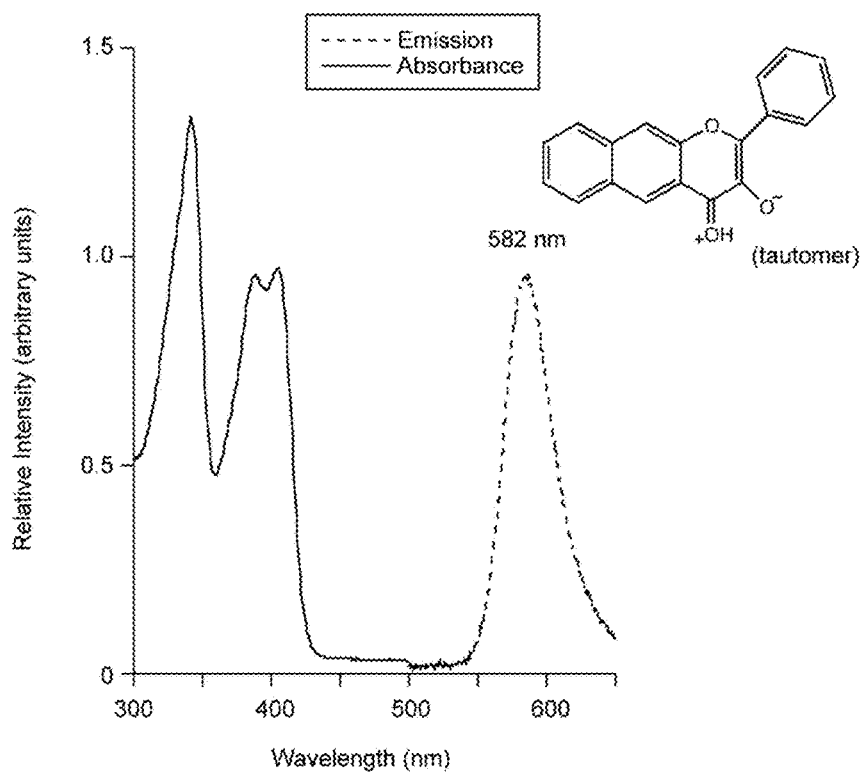
FIG. 6 illustrates absorption and emission spectra of an exemplary compound (compound 5) in dry CH$_3$CN.
Figure 7:
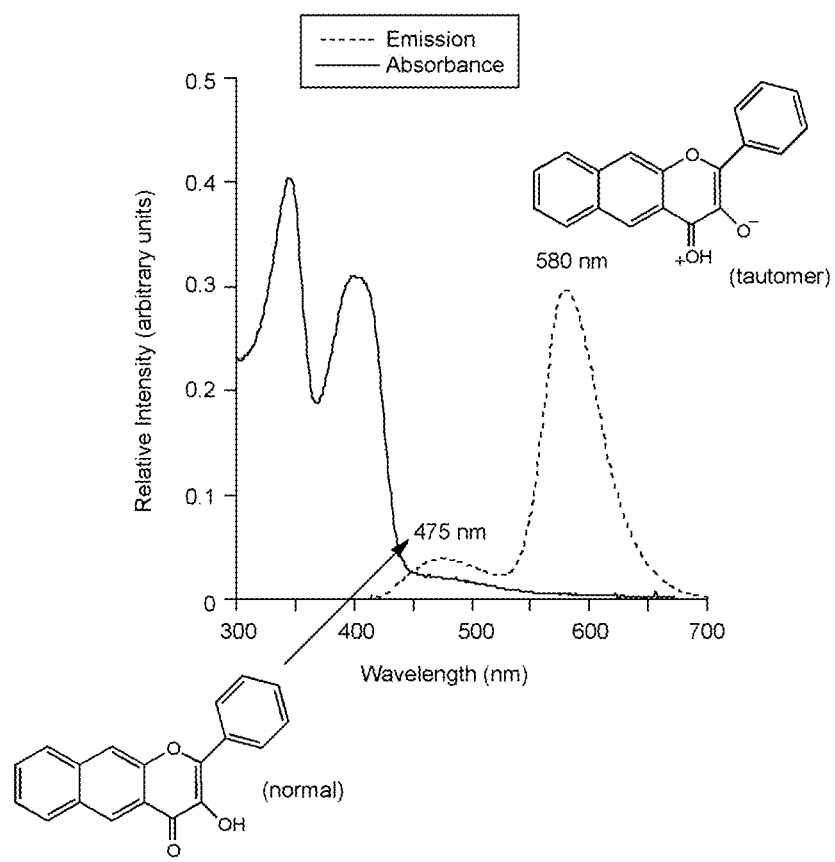
FIG. 7 illustrates absorption and emission spectra an exemplary compound (compound 5) in 1:1 H$_2$O:DMSO.
Figure 8:
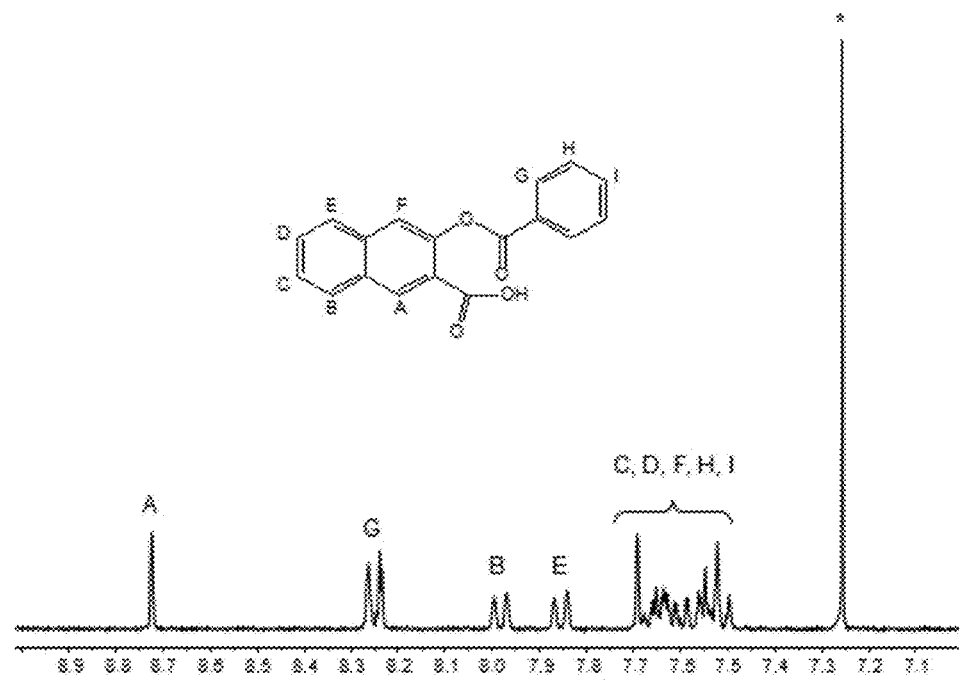
FIG. 8 illustrates $^1$H NMR spectrum an exemplary compound (compound 6) in CDCl$_3$. The * indicates the residual signal of the solvent (CHCl$_3$).
Figure 9:
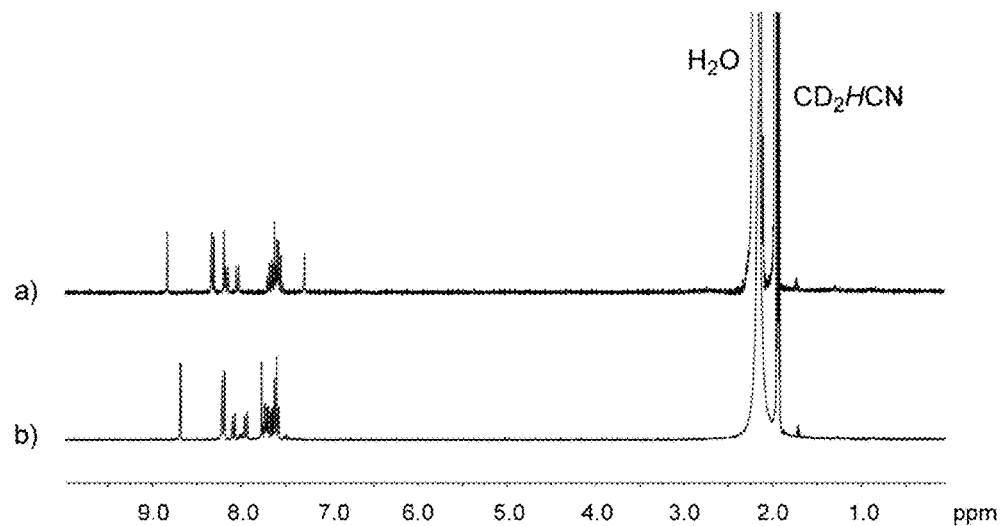
FIG. 9 illustrates various data for exemplary compounds, specifically
Figure 10:
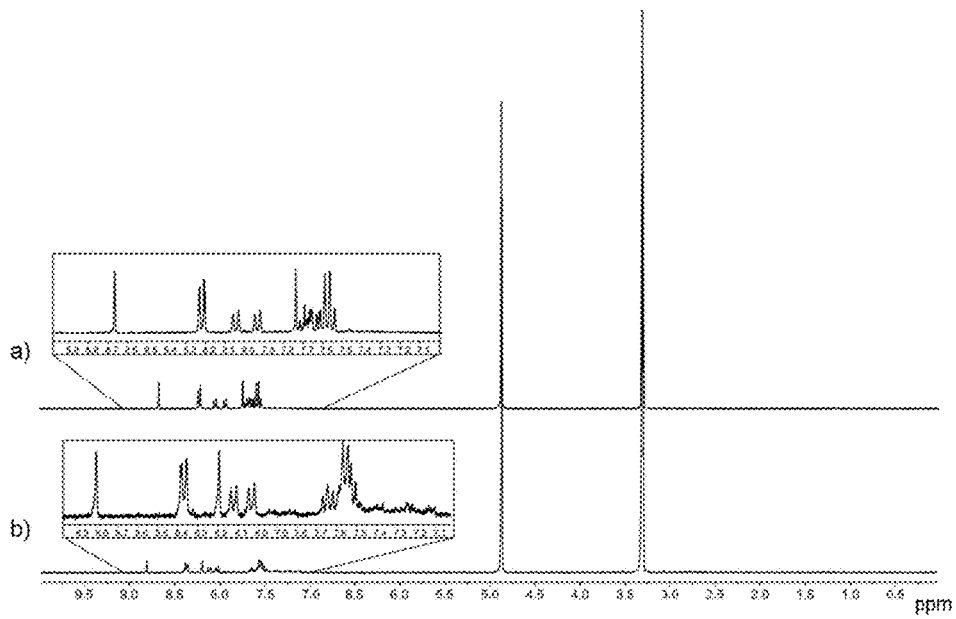
FIG. 10 illustrates various data for exemplary compounds; specifically.
Figure 11:
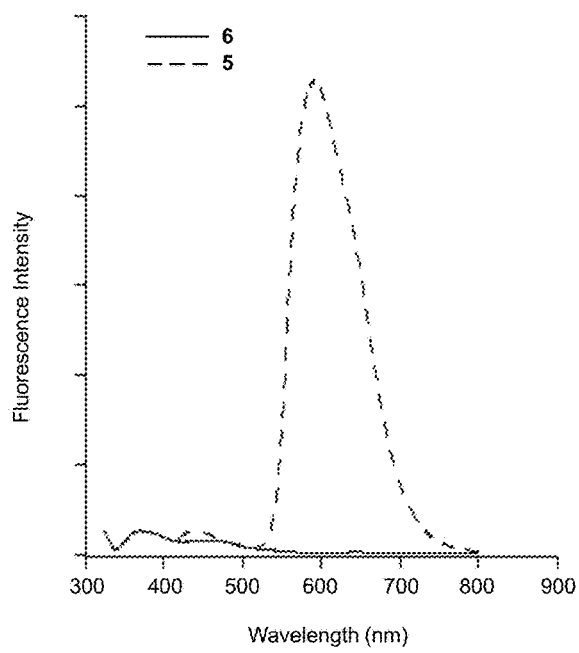
FIG. 11 illustrates emission spectra of exemplary compounds (compounds 5 and 6) in CH$_3$CN under N$_2$ generated upon excitation into the lowest energy absorption maximum (5: 409 nm; 6: 323 nm).

The extended conjugation in 5 produces a red-shift of the absorption features relative to those found for 3-HflH in dry $CH_3CN$ (FIG. 5).[13] The lowest energy band for 5 is found in the visible region at 409 nm ($\epsilon=16,600$ $M^{-1}$ $cm^{-1}$) in $CH_3CN$, whereas in 3-HflH there is no absorption feature above 400 nm. In 1:1 DMSO:$H_2O$, 5 exhibits absorption bands at similar energy, but with lower intensity (FIG. 5). Other flavonols, including quercetin, also exhibit lower intensity absorption features in water-containing solutions.[18] Excitation into any of the absorption features above 300 nm observed for 5 in $CH_3CN$ produces a single broad emission feature centered at 586 nm (FIG. 6). Based on literature precedent for 3-hydroxyflavone, the large Stokes shift (≥177 nm) suggests the formation of an excited state tautomeric form wherein intramolecular proton transfer has occurred to give a zwitterionic species.[19] When dissolved in 1:1 $H_2O$:DMSO and excited in the lowest energy absorption band, 5 exhibits two emission bands at 475 and 582 nm, respectively (FIG. 7). The former is of relative low intensity and likely represents emission from an excited state normal form of the molecule whereas the latter matches the emission feature produced in organic solvent.[19] Solutions of 5 in acetonitrile, 1:1 DMSO:$H_2O$, or 0.1% DMSO:cell culture media (RPMI-1640; pH=7.4) are stable in the presence of ambient $O_2$ for >2 weeks when protected from light. Exposure of an aerobic $CH_3CN$ solution of 5 to visible light (419 nm) results in quantitative CO release (0.96(2) eq) as determined by GC headspace analysis) and the formation of 3-(benzoyloxy)-2-naphthoic acid (6, Scheme 2), which was characterized by $^1H$ NMR (FIGS. 8 and 9), IR, and mass spectrometry. This organic product is pale yellow in color and does not exhibit any emission features in the visible region (FIG. 11). The quantum yield for this CO-release reaction of 5 is 0.007(3). The same reaction occurs in methanol (FIG. 10) and 1:1 $H_2O$:DMSO as determined by $^1H$ NMR and GC head space gas analysis. Appropriate control reactions indicate that both $O_2$ and visible light are needed for the CO release reaction. An $^{18}O_2$ labeling experiment demonstrates that the reaction is dioxygenase-type, with both oxygen atoms from $O_2$ being incorporated into the depside product.

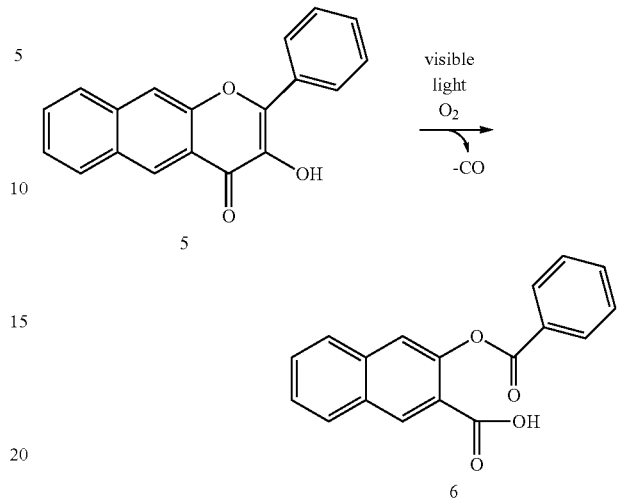

Scheme 2. Photoinduced CO-release reactivity of 5.

Figure 12:
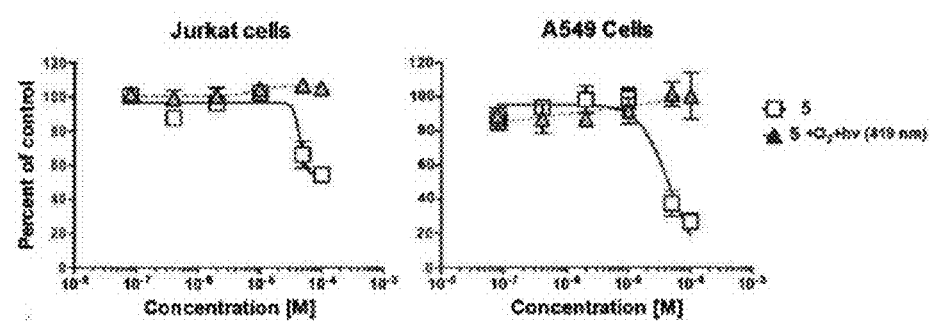
FIG. 12 illustrates plots of human leukemia (Jurkat) and non-small cell lung carcinoma (A549) cell viability versus complex concentration for exemplary compound (compound 5) and its photoinduced reaction product (compound 6). IC$_{50}$ values were determined using a four-parameter nonlinear regression for assays wherein at least a 50% reduction in cell viability was observed, in this case only for A549 cells treated with compound 5 (IC$_{50}$=41.5 μM). Values shown represent the average±SEM of three independently replicated experiments.

Compound 5 exhibits several features that suggest that it could be a useful CO-release agent in biological systems. First, it exhibits only minimal toxicity, as determined by MTT cell viability assays using Jurkat and A549 cells ($IC_{50}$=41.5 uM; FIG. 12), and the organic product remaining following CO-release is completely non-toxic. The low molecular weight, limited number of hydrogen bond donors and acceptors, and calculated octanol-water partition coefficient (log P=3.81)[20] and total polar surface area (TPSA, 50.44)[21], suggest good biological transport characteristics. The $pK_a$ of 5 is expected to be above 9.0 and thus the molecule will remain neutral in a biological environment.[22] The fluorescent nature of 5 makes it trackable in cells prior to CO release. Additionally, compound 5 exhibits antibacterial properties against laboratory strains of E. coli and S. Aureus but only upon irradiation with blue light (Table 1).[23] This suggests that it is the light-induced release of CO that is key to the antibacterial effect. With a well-defined CO-release product (unlike most metal carbonyl-based CORMs), further studies of the antibacterial properties of 5 are clearly warranted.

TABLE 1

Minimum inhibitory concentrations (MIC)* of 5 against various bacterial strains under blue light and under dark conditions.

| | Light Conditions | | | Dark Conditions | | |
|---|---|---|---|---|---|---|
| Compd. | E. coli (ATCC 25922) | S. aureus (ATCC 25923) | S. aureus (ATCC 33591-MRSA) | E. coli (ATCC 25922) | S. aureus (ATCC 25923) | S. aureus (ATCC 33591-MRSA) |
| 5 | 27.8 | 39.4 | 55.5 | † | † | † |

*Unit: μg/mL
† No inhibitory effect against bacterial strain

Figure 13:
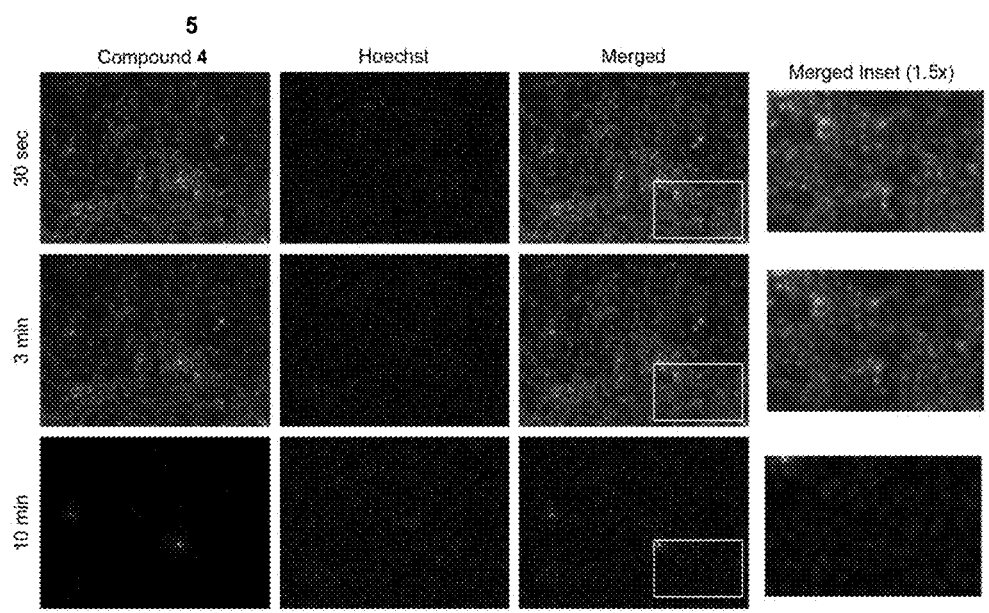
FIG. 13 illustrates fluorescence microscopy of human lung cancer (A549) cells treated with an exemplary compound (compound 5) and then exposed to visible light. Detection of compound 5 (shown above as green) was performed using Zeiss filter set 38: excitation λ of 450-490 nm (BP 470/40 filter) and emission λ of 500-550 nm (BP 525/50 filter). Following a 1 hr incubation with compound 5, cells were excited with visible light for 30 sec, 3 min and 10 min. For localization of the Hoechst dye, a single fluorescence image was acquired at excitation λ at 365 nm; emission λ 420-470 nm (BP 445/50 filter), shown in blue above (repeated down rows for visual comparison). Overlay images indicated that compound 5 was cell permeable, was present in most cells in the field of view, and was localized primarily to the cytoplasm. The apparent loss of fluorescence with increasing length of exposure to visible light suggested photoinduced CO release.
Figure 14:
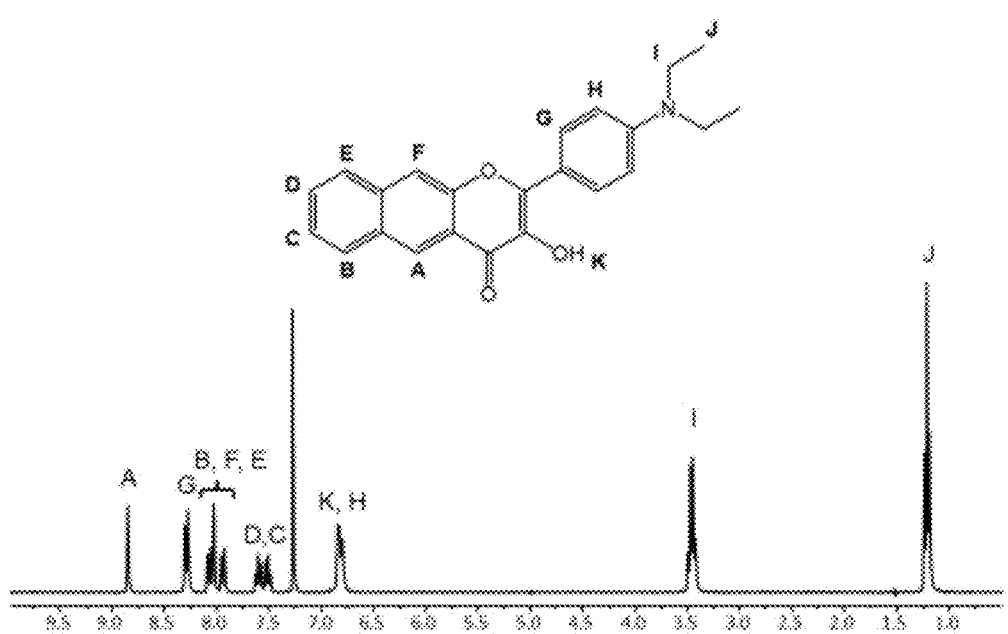
FIG. 14 illustrates $^1$H NMR spectrum an exemplary compound (compound 7) in CDCl$_3$. The * indicates the residual signal of the solvent (CHCl$_3$).
Figure 15:
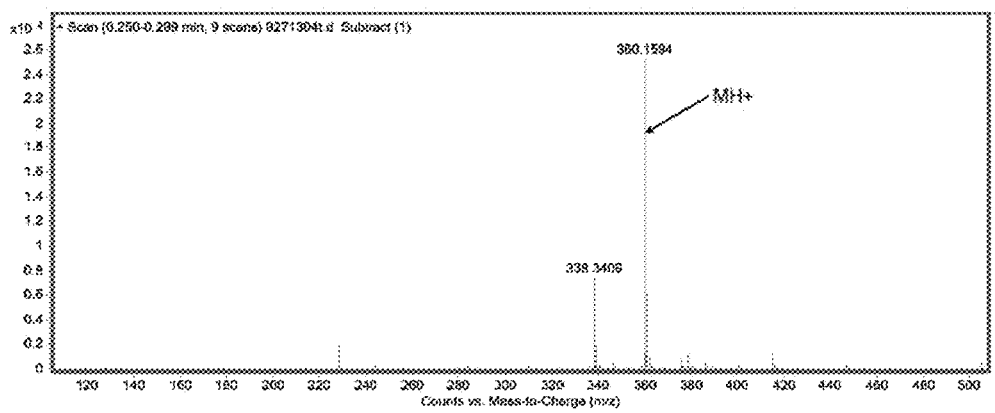
FIG. 15 illustrates ESI/APCI-MS of an exemplary compound (compound 7).
Figure 15:
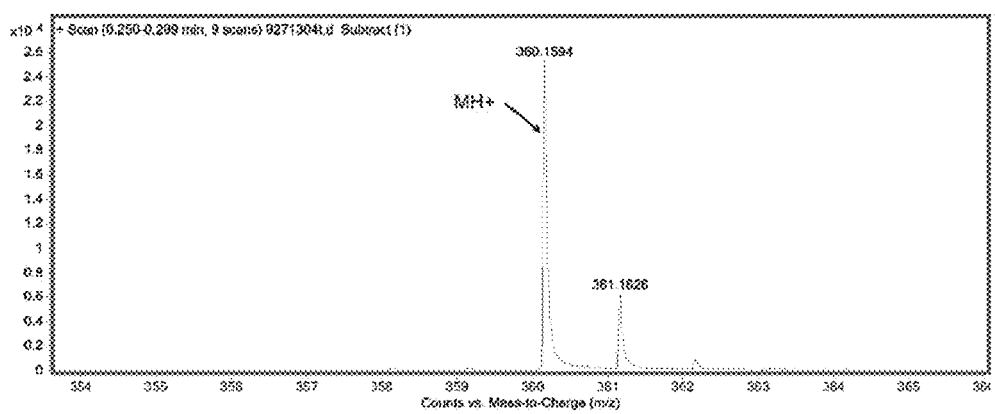
Figure 16:
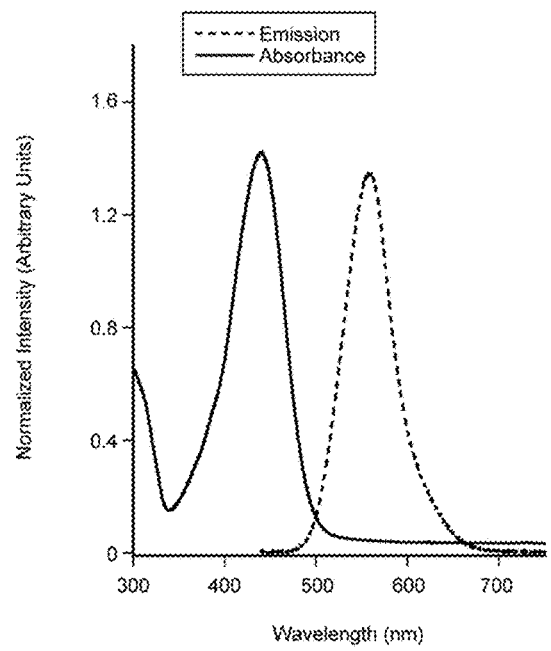
FIG. 16 illustrates absorption and emission spectra of an exemplary compound (compound 7) in dry CH$_3$CN.
Figure 17:
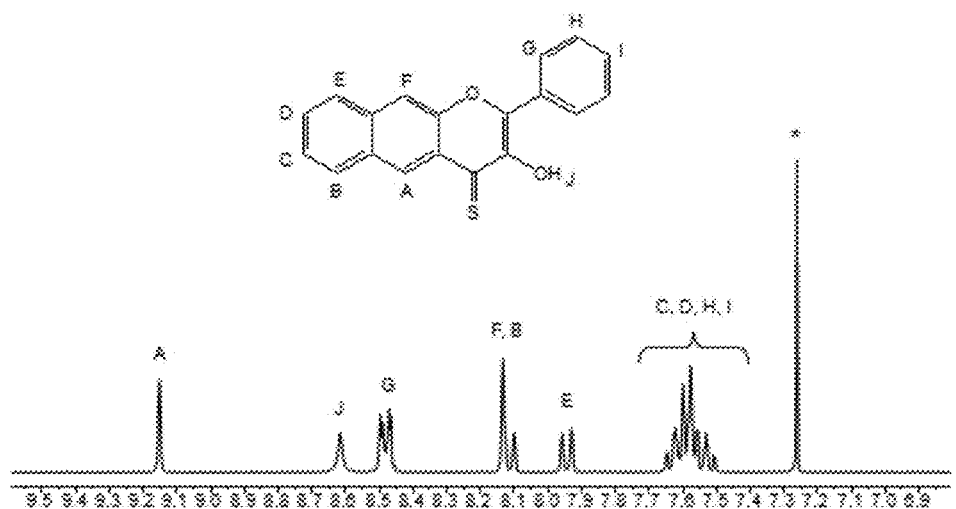
FIG. 17 illustrates $^1$H NMR spectrum an exemplary compound (compound 8) in CDCl$_3$. The * indicates the residual signal of the solvent (CHCl$_3$).
Figure 18:
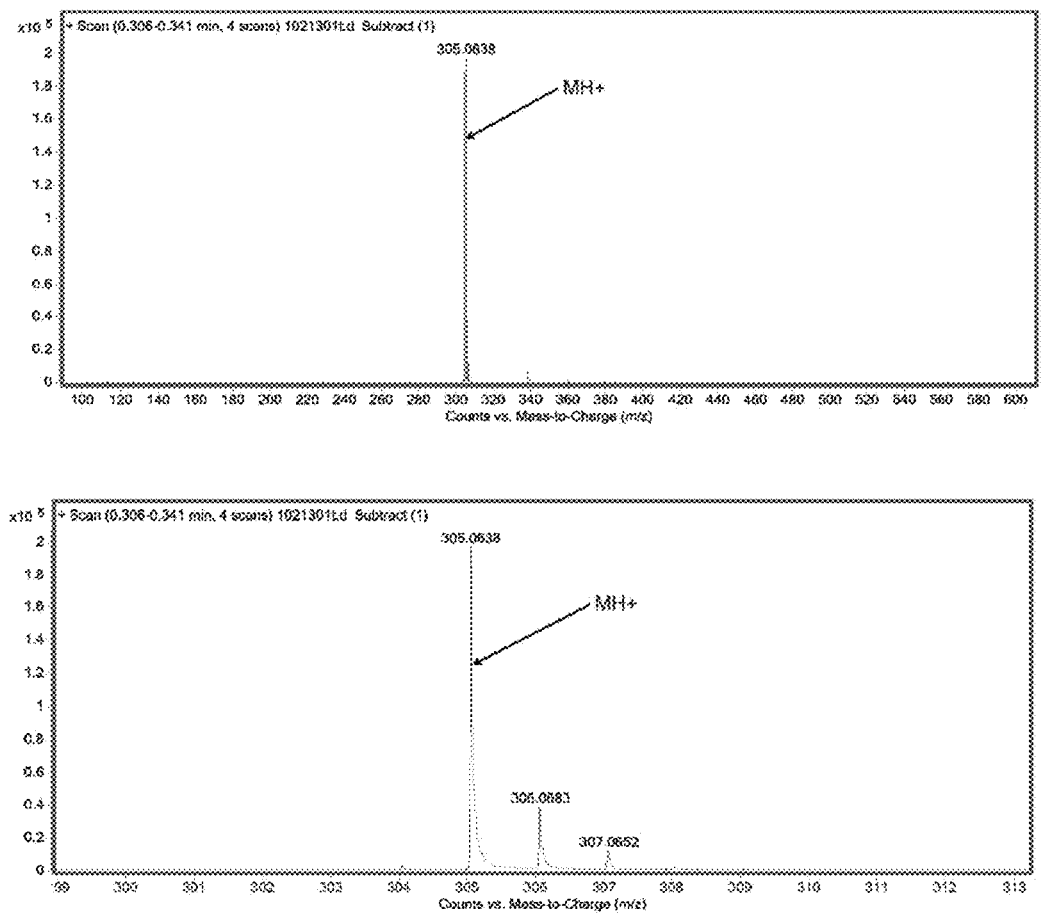
FIG. 18 illustrates ESI/APCI-MS of an exemplary compound (compound 8).
Figure 19:
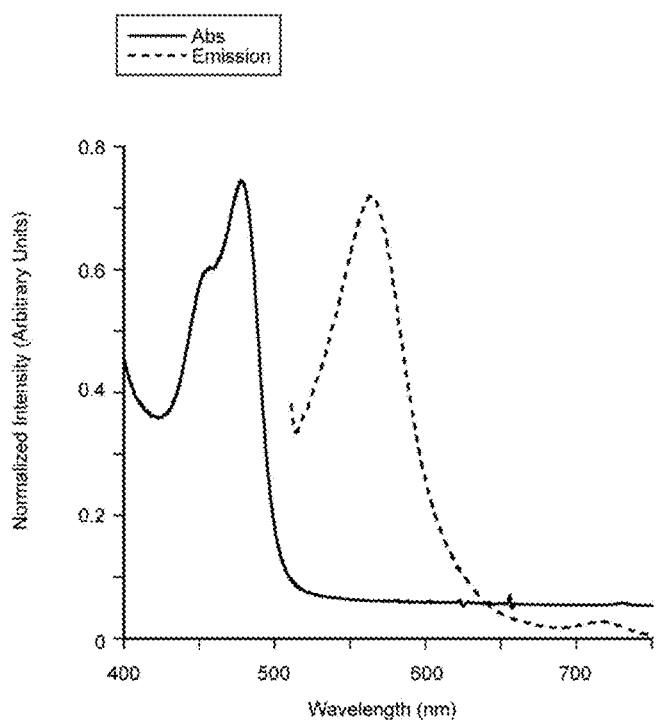
FIG. 19 illustrates absorption and emission spectra of an exemplary compound (compound 8) in dry CH$_3$CN.
Figure 20:
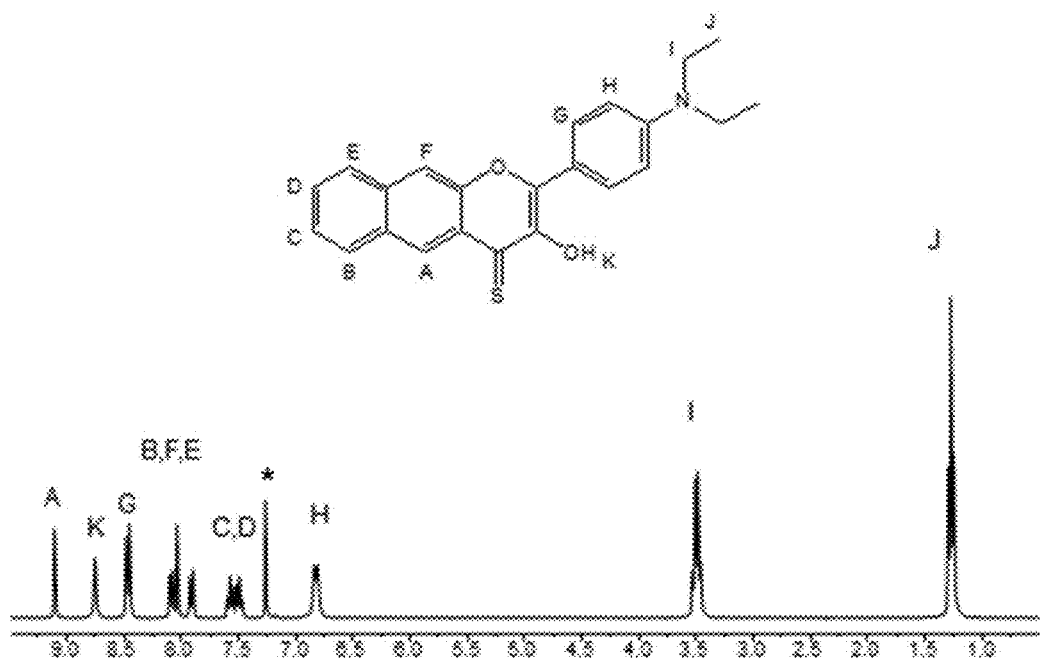
FIG. 20 illustrates $^1$H NMR spectrum an exemplary compound (compound 9) in CDCl$_3$. The * indicates the residual signal of the solvent (CHCl$_3$).
Figure 21:
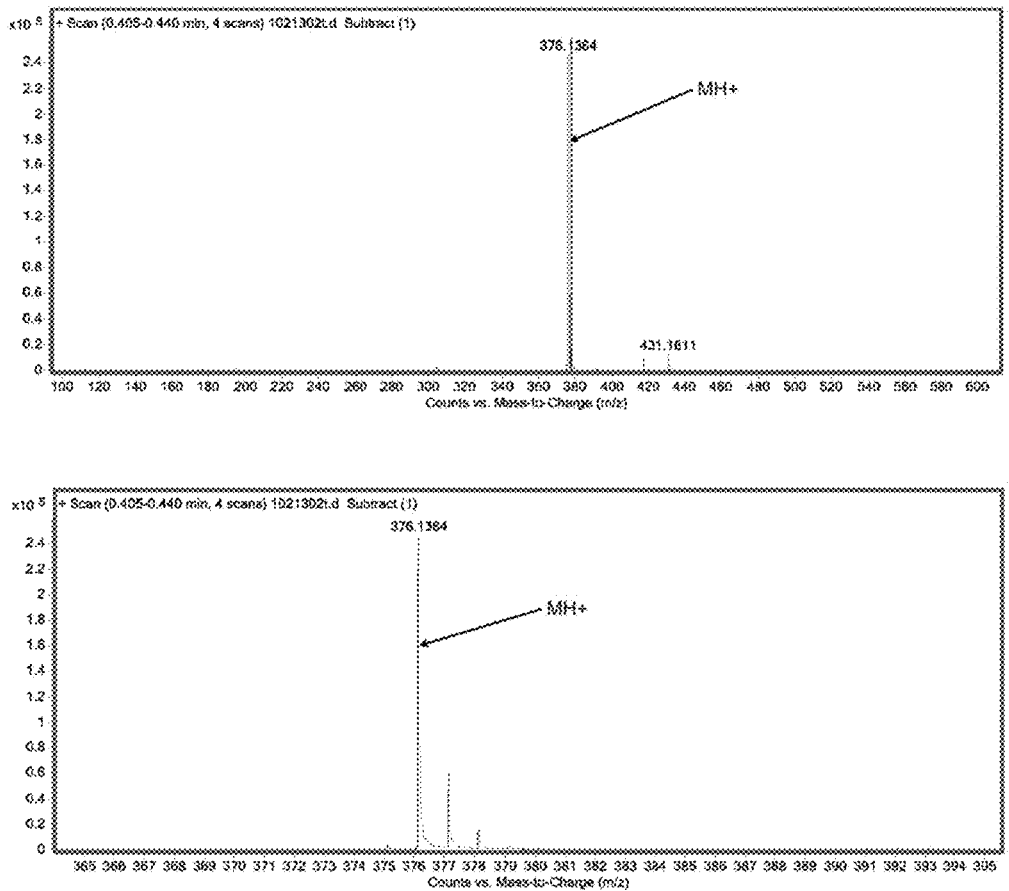
FIG. 21 illustrates ESI/APCI-MS of an exemplary compound (compound 9).
Figure 22:
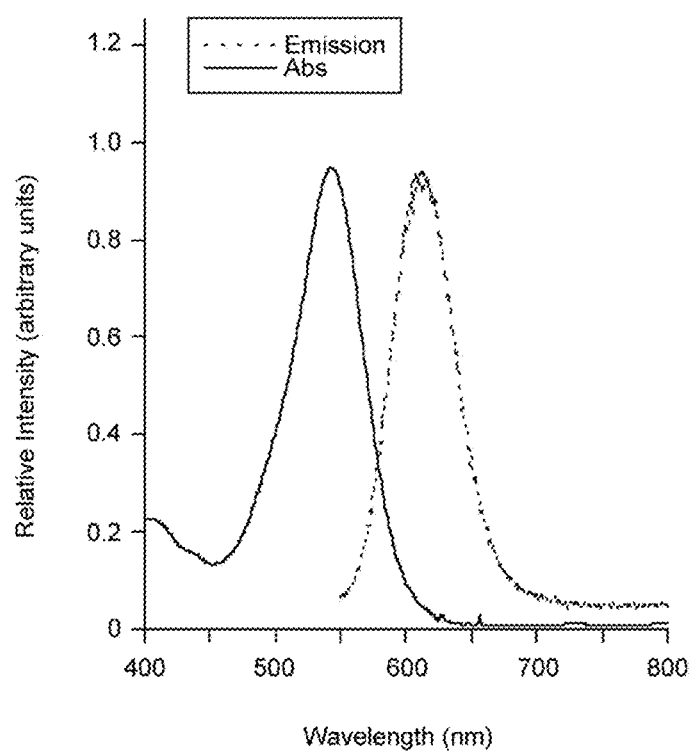
FIG. 22 illustrates absorption and emission spectra of an exemplary compound (compound 9) in dry CH$_3$CN.
Figure 23:
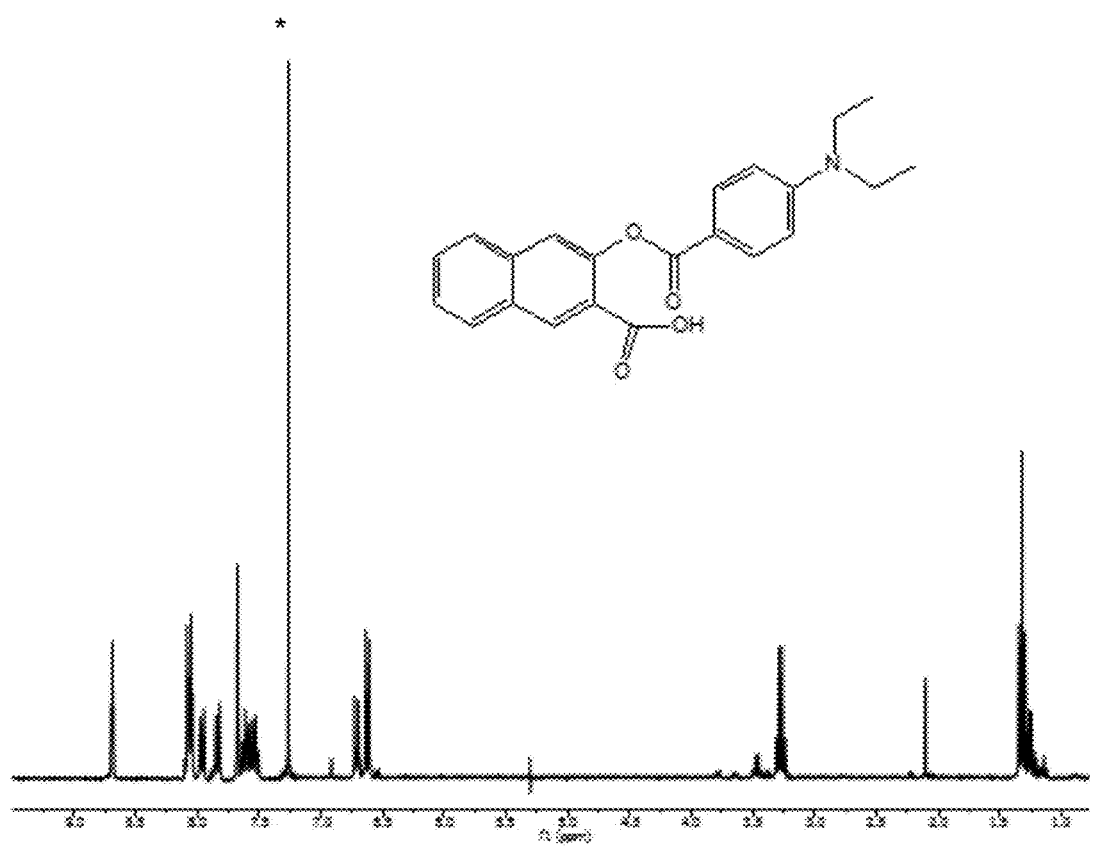
FIG. 23 illustrates $^1$H NMR spectrum an exemplary compound (compound 10) in CDCl$_3$. The * indicates the residual signal of the solvent (CHCl$_3$).
Figure 24:
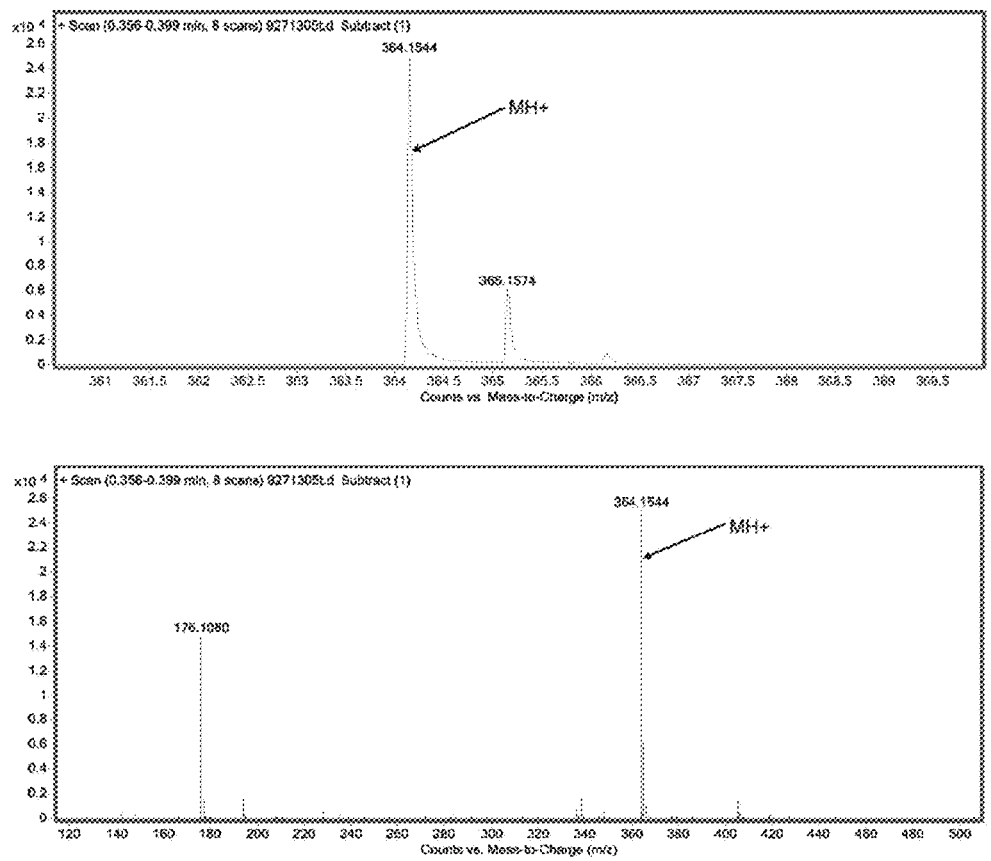
FIG. 24 illustrates ESI/APCI-MS of an exemplary compound (compound 10).
Figure 25:
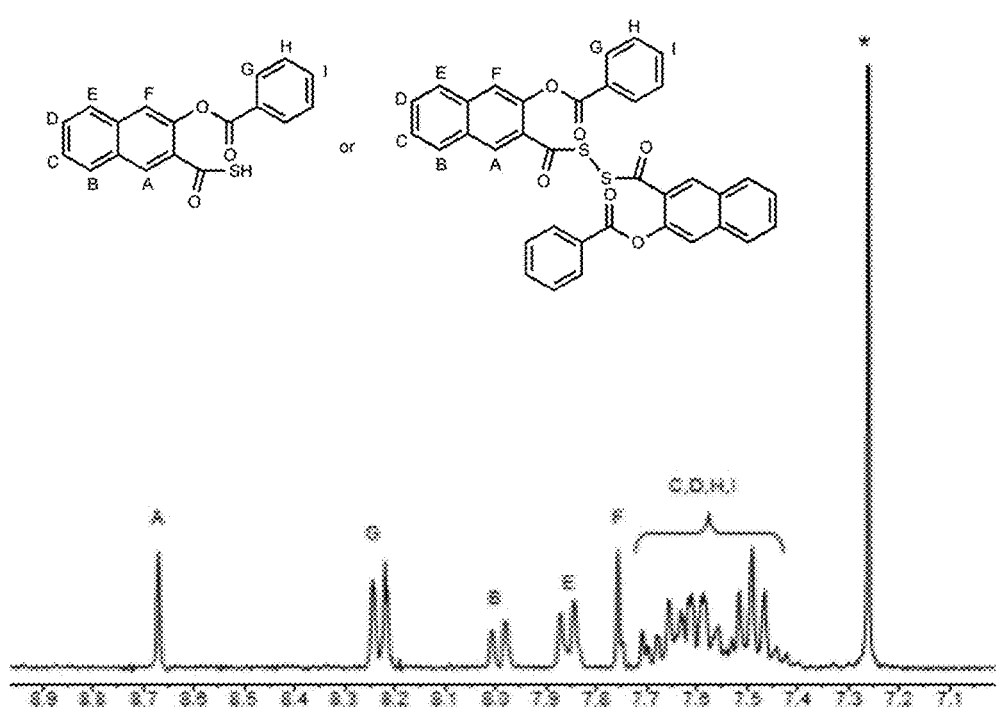
FIG. 25 illustrates $^1$H NMR spectrum an exemplary compound (compound 11) in CDCl$_3$. The * indicates the residual signal of the solvent (CHCl$_3$).
Figure 26:
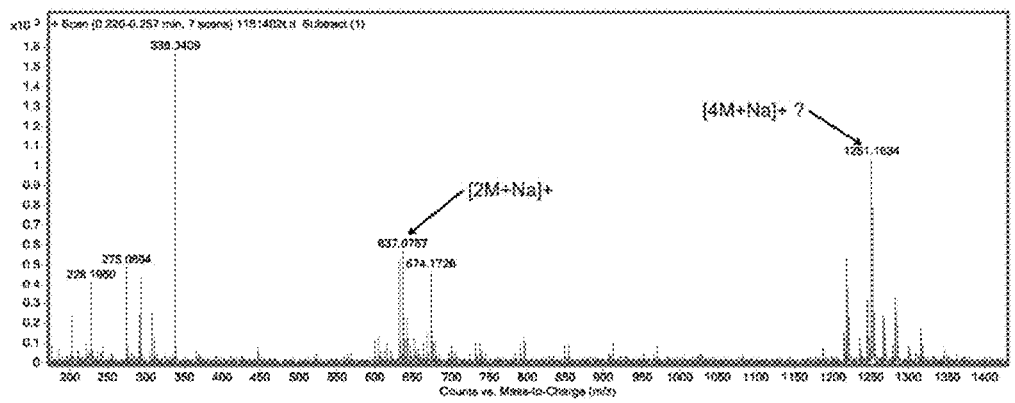
FIG. 26 illustrates ESI/APCI-MS of an exemplary compound (compound 11).
Figure 26:
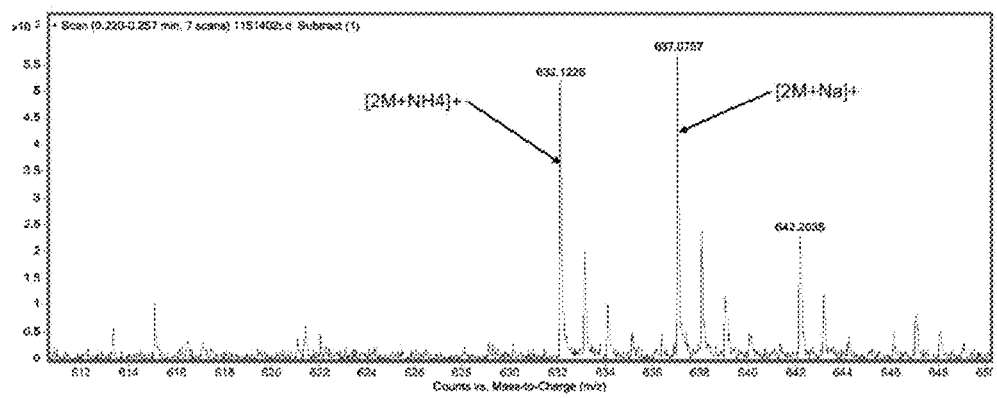

The cellular uptake properties of 5 were evaluated in A549 cells. Following exposure of the cells to Hoechst stain for 10 minutes (to enable visualization of nuclei), followed by exposure to 5 for 1 hour, and washing and fixing the cells, fluorescence images (FIG. 1; FIG. 13) were collected after 30 seconds, 3 minutes, and 10 minutes. The observed green emission at the first two time points provides evidence that 5 is taken up by almost all cells. The compound is not associated with the plasma membrane, but is distributed throughout the cytoplasm and appears to concentrate around the nucleus. Exposure of the cells to visible light results in a decrease in the observed green fluorescence after three minutes, with complete loss after ten minutes. This provides strong evidence for the cleavage of the 3-hydroxy-4-pyrone ring, which is consistent with photoinduced CO-release reactivity within the cells.

Notably, complex 5 binds to bovine serum albumin (BSA), the analog to human serum albumin (HSA), the most abundant carrier protein of blood plasma. Serum albumins are involved in the transportation and distribution of exogenous and endogenous materials in blood.[24] They are capable of binding with various biologically important components (drugs, fatty acids, steroids, dyes etc.). Using fluorescence quenching studies, we have determined that 5 binds to a single binding site on BSA with an affinity ($3.2 \times 10^3$ $M^{-1}$) which is lower than is typically observed for naturally-occurring flavonols (e.g. quercetin $3.65 \times 10^7$)[25] but that is similar to some drug/BSA interactions. For example, the anticancer drug doxorubicin binds to BSA with an affinity of $7.3 \times 10^3$ $M^{-1}$.[26] Competitive binding studies with warfarin and ibuprofen, as well as molecular docking studies using AutoDock Vina[27], demonstrate that 5 likely binds at site 1 (subdomain II A) of BSA via hydrogen bonding interactions.[28] Notably, binding of 5 to BSA results in only a two-fold decrease in the rate of light induced CO-release from this compound.

A key feature of the structural motif of 5 that distinguishes it from those of all previously reported for organic photo-CORMs is the ease with which structural modifications can be introduced to tune physical properties. For example, to red-shift absorption features toward the therapeutic window, a dialkylamino substituent can be incorporated on the phenyl ring, or the carbonyl oxygen can be substituted with sulfur. Dialkylamino-substituted flavonols have been previously shown to have excited state fluorescent properties that make them very useful as environment-sensitive probes in biological systems.[29] However, neutral flavonols of this type have not been previously shown to exhibit photoinduced CO-releasing reactivity. Flavothiones, have been reported to undergo $O_2$-dependent photodegradation to give non-toxic byproducts, but these reactions have not been fully explored in terms of product identification.[30]

Molecules 7-9 were prepared using standard synthetic methods and were isolated in analytically pure form via precipitation.

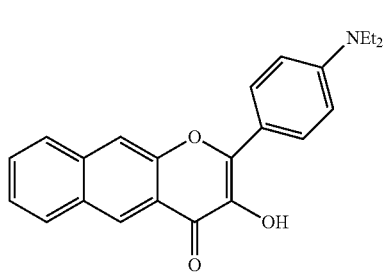

7

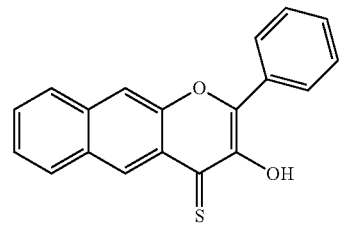

8

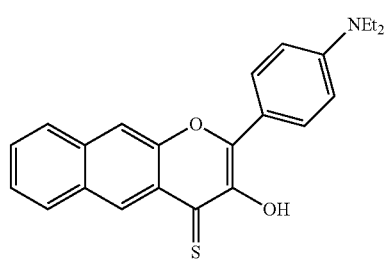

9

Figure 2:
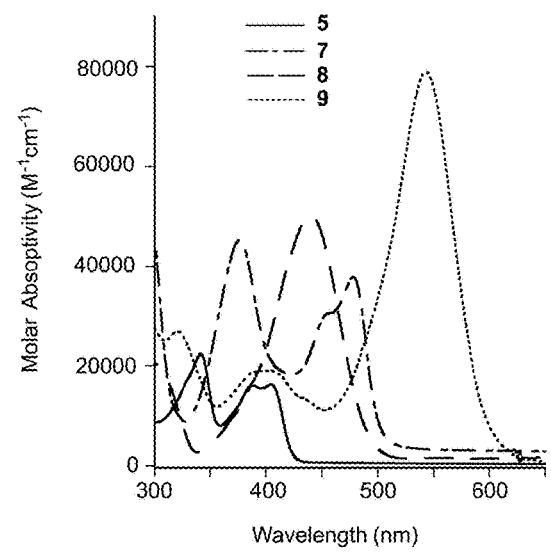
FIG. 2 illustrates absorption spectra of exemplary compounds (5 and 7-9) in CH$_3$CN.
Figure 3:
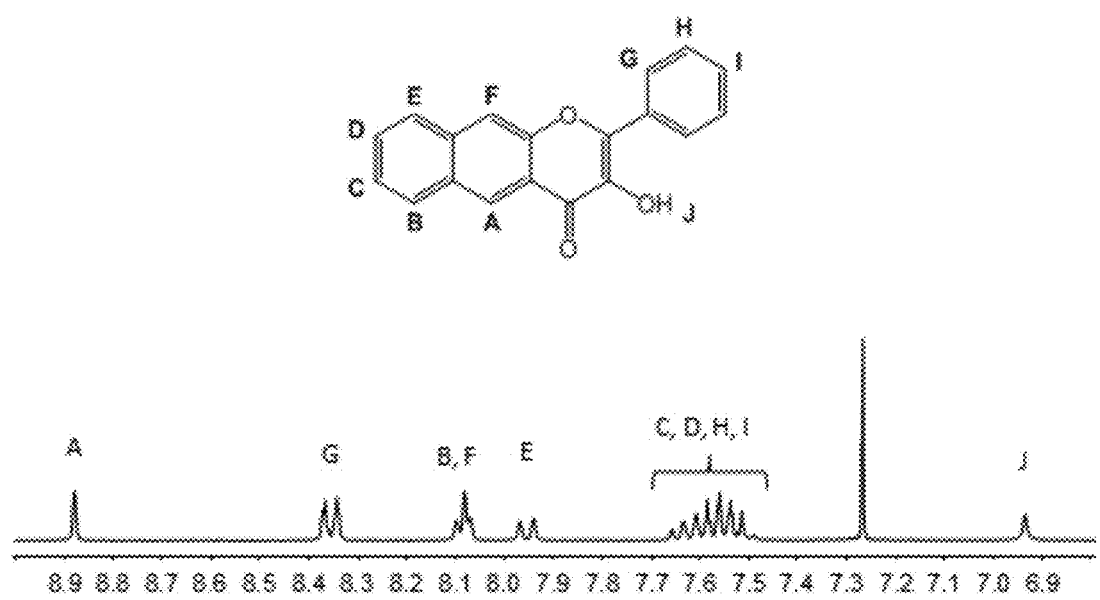
FIG. 3 illustrates $^1$H NMR spectrum of an exemplary compound (compound 5) in CDCl$_3$. The * indicates the residual signal of the solvent (CHCl$_3$).

Each compound was characterized by elemental analysis, UV-vis, fluorescence, IR, and mass spectrometry (FIG. 14-22). These molecules exhibit red-shifted absorption features and higher molar absorptivity values than was observed for 5 (FIG. 2). When aerobic $CH_3CN$ solutions of 7-9 are exposed to visible light (7,8: 419 nm; 9: >546 nm) quantitative CO release occurs (Table 2). For 7 and 8, dioxygenase-type organic products akin to the reaction of 5 were identified by $^1H$ NMR, IR, and mass spectral analysis (FIGS. 23-26). The organic products resulting from photoirradiation of 9 remain under investigation. The quantum yields associated with these reactions are significantly enhanced in the thioflavone derivatives. Photoinduced CO-release also occurs in when 7-9 are dissolved in other solvents, including DMSO and 1:1 DMSO:$H_2O$ solution.

TABLE 2

CO and quantum yields for the reactions of 5 and 7-9 with $O_2$ in the presence of visible light.

| Compound | eq. CO[c] | Φ[c] |
|---|---|---|
| 5[a] | 0.96(2) | 0.007(3) |
| 7[a] | 0.99(1) | 0.006(1) |
| 8[a] | 1.01(1) | 0.426(3) |
| 9[b] | 1.01(1) | 0.20(1) |

[a]Measured using 419 nm irradiation.
[b]Measured using >546 nm irradiation.
[c]Reported values are the average of three independent trials.

TABLE 3

Antioxidant properties of 5 and 7-9 in methanol measured using DPPH assay.

| Compound | IC$_{50}$ (methanol) |
|---|---|
| 3-hydroxyflavone | 675 ± 9 |
| quercetin | 15 ± 1 |
| 5 | 16 ± 2 |
| 7 | 10 ± 1 |
| 8 | 7 ± 1 |
| 9 | 6 ± 1 |

Notably, compounds 5 and 7-9 exhibit antioxidant properties similar to the well-known and commercially available antioxidant quercetin (Table 3).[31]

Figure 27:
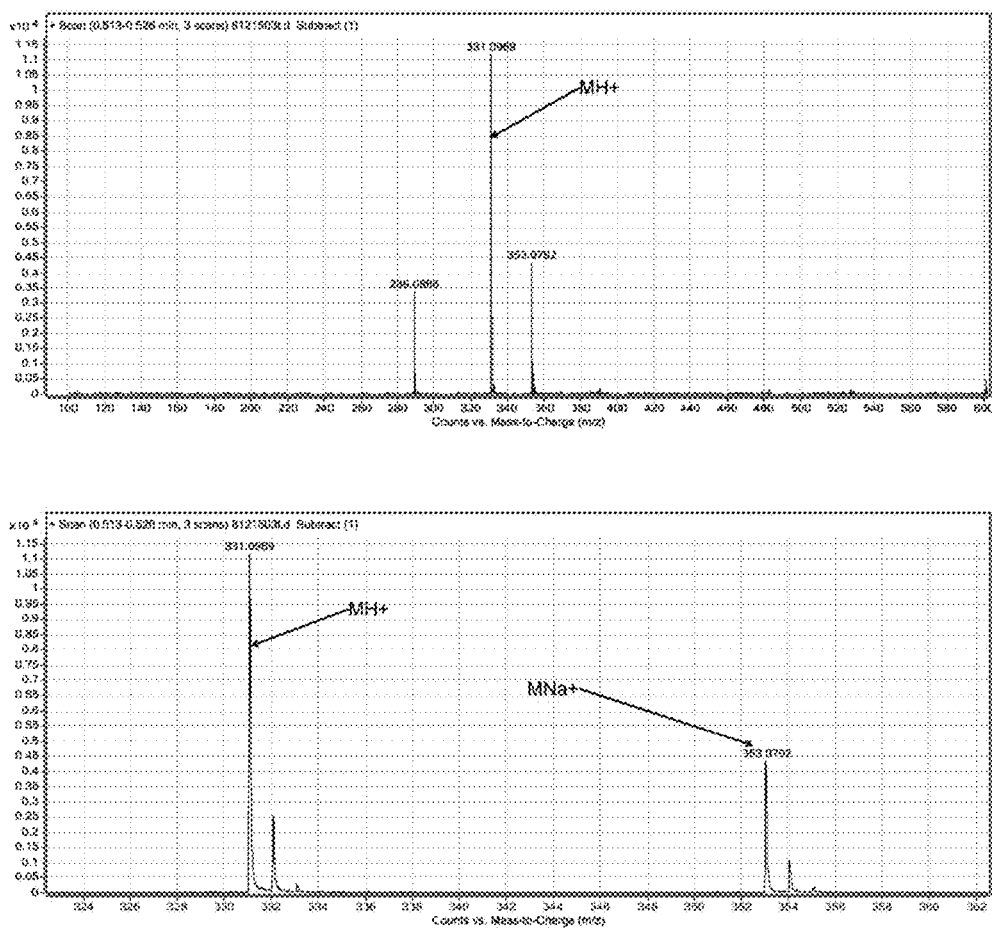
FIG. 27 illustrates ESI/APCI-MS of an exemplary compound (compound 12).
Figure 28:
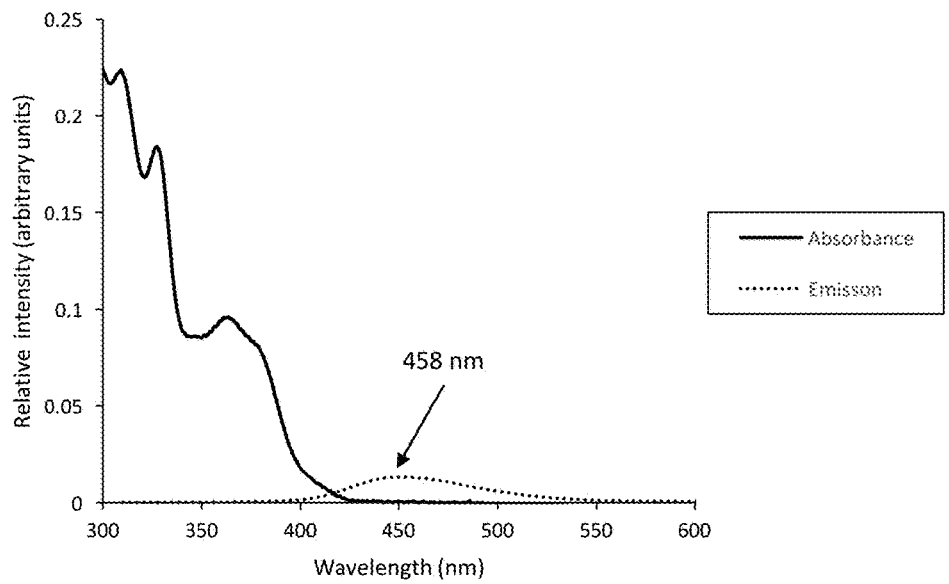
FIG. 28 illustrates absorption and emission spectra of an exemplary compound (compound 12).

Introduction of an ester protecting group to 5 produces compound 12 (Scheme 3), which has been characterized by $^1$H NMR (FIG. 27), IR, UV-vis, mass spectrometry (FIG. 28), elemental analysis and X-ray crystallography. Compound 12 represents an approach toward adding a second triggering mechanism for CO-release from 5.[32] For example, under at neutral pH, compound 12 is significantly more stable to visible light that 5. However, under slightly basic conditions, or in the presence of esterase, it is anticipated that the ester protecting group will be hydrolyzed thus allowing access to 5.

Scheme 3. Ester-protected form of 5; proposed deprotection in presence of base or esterase.

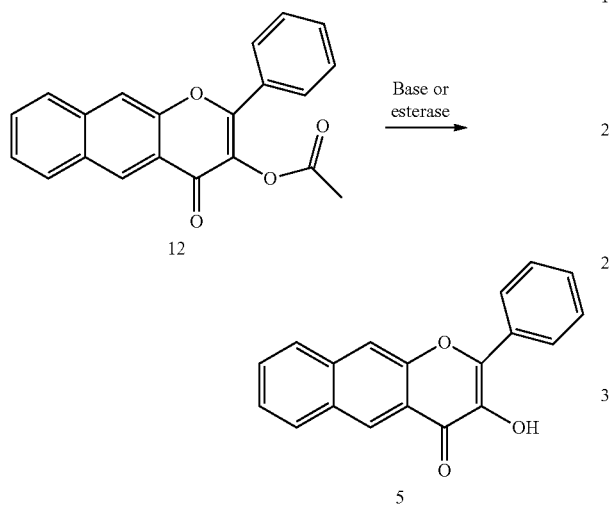

Figure 29:
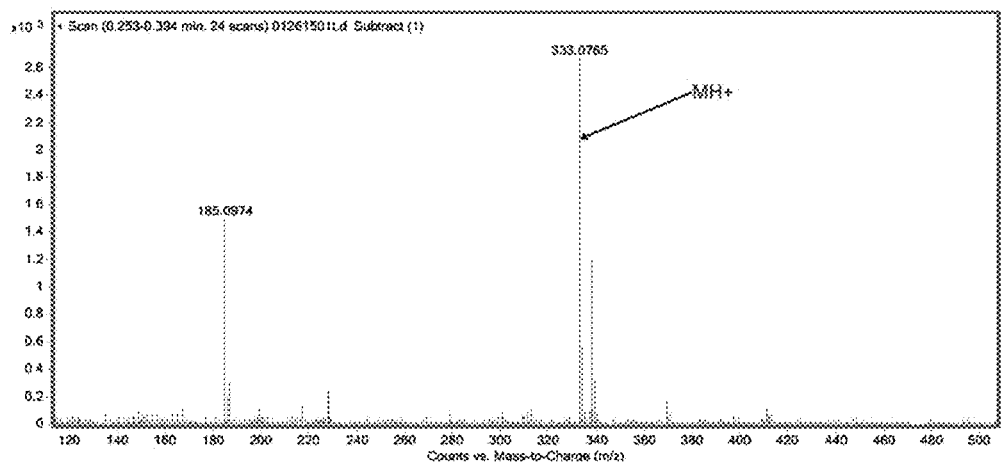
FIG. 29 illustrates ESI/APCI-MS of an exemplary compound (compound 13).
Figure 30:
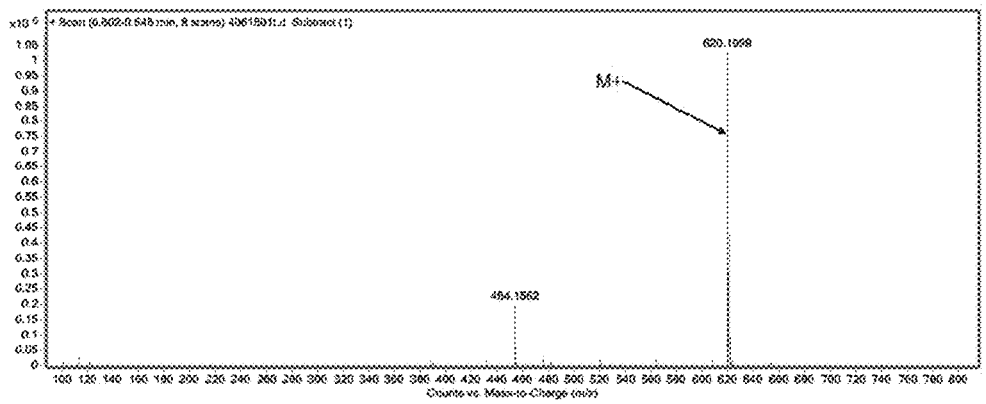
FIG. 30 illustrates ESI/APCI-MS of an exemplary compound (compound 14).

A tremendous advantage of the synthetic route leading to 5 is that structural modifications on the phenyl substituent can be introduced by changing the aldehyde used in the synthesis. Hence the carboxyl-appended 13 was prepared as shown in Scheme 4 and characterized by $^1$H NMR (FIG. 29), IR, and mass spectrometry. Compound 13 serves as a precursor to which tails can be attached for targeting of CO delivery to specific locations of the cell. For example, as shown in Scheme 5, coupling of 13 with amino-appended phosphonium derivatives enables preparation of a new family of compounds (14-16) for targeting of CO delivery to mitochondria. This is an important, timely application of CO-releasing molecules as the detailed molecular mechanisms by which CO modulates mitochondrial function are currently not well defined.[33] The triphenyl phosphonium tail is a well known approach toward delivery "payloads" to mitochondria.[34] Structures 14-16 (Scheme 5) have been assembled using EDC coupling reactions. $^1$H NMR and mass spectrometry (14, FIG. 30) provide evidence for the proposed formulations.

Scheme 4. Preparation of carboxy-appended derivative 13.

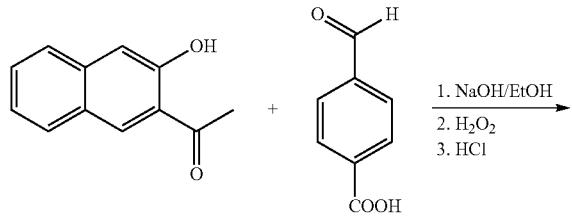

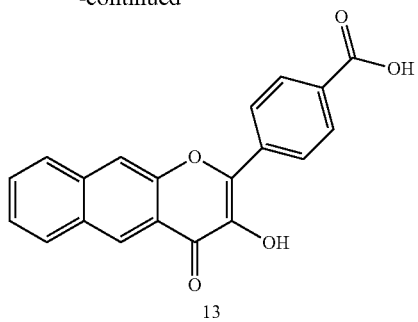

Scheme 5. Preparation of phosphonium-tailed derivatives 14-16 for CO delivery to mitochondria.

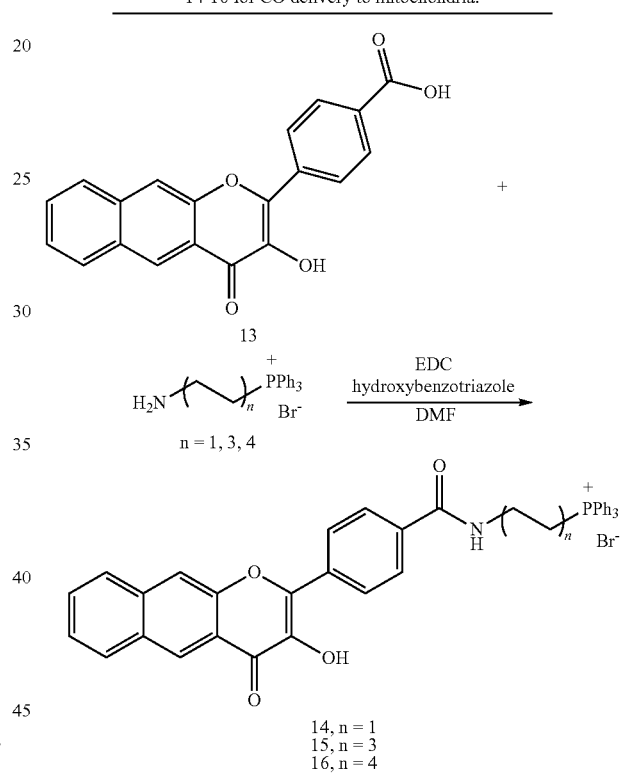

The new structural motif reported herein offers many advantages in terms of photoCORM design. Compounds based on the 3-hydroxyflavone motif can be prepared in multigram quantities and isolated in analytically pure form in moderate to high yields. Compounds 5, 7-9, and 12-16 are soluble in organic solvents ($CH_3CN$, MeOH, DMSO) as well as aqueous DMSO. Solutions of these compounds are stable with respect to $O_2$ for weeks when protected from light. CO release is triggered by the introduction of visible light, the wavelength of which can be tuned through structural modification of the molecule. A representative example of this family of compounds (5) exhibits minimal toxicity and its organic byproduct following CO release is completely non-toxic. The fluorescent nature of 5 makes it trackable in cells. The observed photoinduced reactivity of 7-9 demonstrates that structural modifications can be made to the flavonol without loss of the CO-release capability. This suggests that this family of compounds could be expanded to address any issues encountered (e.g. solubility or toxicity), and enable targeting. Further evaluation of the applications of these novel molecules and analogs for CO-release in biological systems are in progress.

The following examples are illustrative only and are not intended to limit the disclosure in any way.

EXAMPLES

Chemicals and Reagents

All chemicals and reagents were obtained from commercial sources and used as received unless otherwise noted. Anaerobic procedures were performed under $N_2$ in a VAC Atmosphere glovebox. Solvents for glovebox use were dried according to published methods and distilled under $N_2$.[35]

Physical Methods.

$^1$H and $^{13}$C{$^1$H} NMR spectra (in ppm) were collected using JEOL ECX-300 MHz spectrometer and are referenced to the residual solvent peak in $CDCl_3$ ($^1$H: 7.26 (singlet) ppm; $^{13}$C 77.16 (singlet) ppm) or DMSO-$d_6$ ($^1$H: 2.50 ppm (quintet)). J values are given in Hz. IR spectra were collected using a Shimadzu FTIR-8400 as potassium bromide pellets. UV-vis spectra were recorded at ambient temperature using a Hewlett-Packard 8453A diode array spectrophotometer. Fluorescence emission spectra were collected using a Shimadzu RF-530XPC spectrometer in the range of 400-800 nm, with the excitation wavelength corresponding to the absorption maxima of the molecules. The excitation and emission slit widths were set at 1.5 nm for all molecules. Mass spectral data was collected at the Mass Spectrometry Facility, University of California, Riverside. ESI/APCI mass spectra were recorded on an Agilent LCTOF (2006) with a Windows XP based operating system. Elemental analyses were performed by Atlantic Microlab, Inc., Norcross, Ga., using a PE2400 automatic analyzer or at Robertson Microlit Laboratories, Ledgewood, N.J. using a Perkin Elmer CHN Analyzer Model 2400, Series II. A Rayonet photoreactor equipped with either RPR-4190A or white light lamps with 546 nm cutoff filters were used for all photochemical reactions. Quantum yields were determined using potassium ferrioxalate or potassium reinekate as standards to measure photon flux.[36] Carbon monoxide was quantified as previously described.[37]

1-(3-hydroxynaphthalen-2-yl)ethanone 3-hydroxy-2-naphthoic acid (1.8818 g, 10 mmol) was dissolved in dry, freshly distilled THF (40 mL). This solution was purged with $N_2$ and subsequently cooled to 0° C. using an ice bath. Methyllithium (30 mmol, 18.7 mL, 1.6 M in hexanes) was then slowly added in aliquots via air-tight syringe. The reaction was allowed to stir at 0° C. for 3 hours and then quenched with 0.5 M HCl dropwise until any frothing ceased. The THF was then removed under reduced pressure and 0.5 M HCl (60 mL) was added to the residue. The acidic aqueous solution was then extracted using dichloromethane (50 mL×3). The combined organic fractions were dried over sodium sulfate. The solvent was then removed under reduced pressure yielding the product as a bright yellow solid (1.84 g, 99%). $^1$H NMR ($CDCl_3$, 300 MHz) δ 11.54 (s, 1H), 8.35 (s, 1H), 7.79 (d, J=6.0 Hz, 1H), 7.65 (d, J=6.0 Hz, 1H), 7.50 (t, J=5.1 Hz, 1H), 7.32 (t, J=5.1 Hz, 1H), 7.24 (s, 1H), 2.78 (s, 3H) ppm. $^{13}$C NMR ($CDCl_3$, 100 MHz) 204.9, 157.3, 138.4, 133.7, 129.8, 129.5, 127.0, 126.4, 124.2, 121.5, 112.4, 27.1 ppm (12 signals expected and observed). Melting point 111-113° C. The $^{13}$C NMR and melting point data are consistent with reported literature values.[38]

3-Hydroxy-2-phenyl-benzo[g]chromen-4-one (5)

Sodium hydroxide (21 mL. 5M, 104 mmol) was added to a suspension of 1-(3-hydroxynaphthalen-2-yl)ethanone (3.90 g, 21 mmol) in ethanol (60 mL) and allowed to stir for 30 minutes at room temperature. Benzaldehyde (2.14 mL, 21 mmol) was added to the reaction and the resulting mixture was stirred for 5 hours resulting in the formation of a dark red solution. The reaction was then cooled to 0° C. in an ice bath, hydrogen peroxide (7.6 mL, 30%) was added drop-wise, and the resulting mixture was stirred overnight while warming to room temperature. Acidification of the solution to pH=6.5 with 0.5 M HCl resulted in the formation of a bright yellow precipitate which was isolated by filtration and washed with ethanol (3.74 g, 62%). $^1$H NMR ($CDCl_3$, 300 MHz) δ 8.88 (s, 1H), 8.35 (d, J=5.4 Hz, 2H), 8.08 (t, J=3.6 Hz, 2H), 7.95 (d, J=6.3 Hz, 1H), 7.67-7.45 (m, 5H), 6.93 (s, 1H) ppm. $^{13}$C NMR ($CDCl_3$, 100 MHz) 174.6, 151.7, 145.8, 137.3, 136.1, 131.4, 130.5, 130.0, 129.6, 129.0, 128.8, 128.2, 127.4, 126.7, 126.0, 120.1, 114.4 ppm (17 signals expected and observed). FTIR (KBr, cm$^{-1}$) 3290 ($v_{O-H}$), 1596 ($v_{C=O}$). UV-vis ($CH_3CN$, nm) (ε, M$^{-1}$ cm$^{-1}$) 409 (16,600), 392 (15,900), 345 (22,800). Melting point 208-210° C. Anal. Calc. $C_{19}H_{12}O_3$: C, 79.16; H, 4.20. Found: C, 78.96; H, 4.23. ESI/APCI-MS m/z (relative intensity) 289.0866, calc. 289.0859 ([MH]$^+$, 100%).

Photoreactivity of 4 in the Presence of $O_2$. Production of 3-(Benzoyloxy)-2-Naphthoic Acid (6).

A solution of 5 (~0.05 mmol) in 5.0 mL $CH_3CN$ was placed in a 50 mL round bottom flask under air. The solution was then placed in a Rayonet photoreactor equipped with 419 nm lamps and was irradiated until the reaction was determined complete as evidenced by the disappearance of the lowest energy absorption band. The solvent was then removed under reduced pressure yielding an off-white solid (100%). $^1$H NMR ($CDCl_3$, 300 MHz) δ 8.73 (s, 1H), 8.25 (d, J=7.5, 2H), 7.98 (d, J=7.8, 1H), 7.86 (d, J=7.8, 1H), 7.72-7.46 (m, 6H) ppm. FT-IR (KBr, cm$^{-1}$) 1743 ($v_{C=O}$). ESI/APCI-MS, m/z (relative intensity) 293.0811, calc. 293.0808 ([MH]$^+$, 83%).

$^{18}$O-Labeling Studies.

Aliquots of $^{18}O_2$ were transferred into a frozen $CH_3CN$ solution of 5 in a 100 mL solvent transfer flask followed by irradiation at 419 nm and removal of the solvent under reduced pressure. The product was analyzed by mass spectrometry.

Dark Control Reaction.

A solution of 5 in $CD_3CN$ (~3 mM) was prepared in air under minimal red light and placed in an NMR tube. The NMR tube was then covered with foil, placed in a photo reactor, and irradiated using 419 nm lamps for 24 hours. Evaluation of the solution by $^1$H NMR indicated that no reaction had occurred.

Anaerobic Control Reaction.

A solution of 5 in $CD_3CN$ (~3 mM) was prepared under $N_2$ in a glove box and placed in an NMR tube. The NMR tube was then placed in a photo reactor and irradiated using 419 nm lamps for 24 hours. Evaluation of the solution by $^1$H NMR indicated that no reaction had occurred.

Cell Culture and Viability Assays.

Jurkat (JM) cells were maintained as previously described by Shorey et al.[39] A549 human adenocarcinoma cells (ATCC, Manassas, Va.) cells were grown in DMEM/Ham's F-12 1:1 mixture medium supplemented with 10% charcoal-stripped, heat-inactivated fetal bovine serum (FBS; Caisson Laboratories, Logan, Utah) in a humidified incubator at 37° C. with 5% $CO_2$. Cytotoxicity was determined by the colorimetric MTT [3-(4,5-dimethyl-2-thiazolyl)-2,5-diphenyl-2H-tetrazoluim bromide] assay as previously describe.[40] Briefly, $2.1 \times 10^3$ cells/ml for A549 cells or $1 \times 10^5$ cells/ml for Jurkat cells. Test compounds were prepared in DMSO, then added to culture media for a maximum final DMSO concentration not greater than 0.1% (v/v). After addition of test compounds at concentrations ranging from 80 nM to 100 µM, cells were incubated for 24 h in the dark, then treated with MTT to assess cell viability as outlined previously.[40] All experiments were independently replicated three times, and each experimental treatment was performed in triplicate.

Fluorescence Microscopy.

A549 cells were maintained in culture as described above, then seeded into seeded into Millicell E-Z-Slide culture chambers (EMD Millipore, Billerica, Mass.) at an initial density of $7.5 \times 10^4$ cells/cm$^2$ and allowed to adhere to the chamber slides for 24 hr. The cells were then treated for 1 hr with the nuclear dye Hoechst 33342 (0.5% v/v) for 10 min, followed by three washes with plain culture media to remove residual dye. All of incubation and wash steps described below were performed in the dark with minimal light exposure. A 100 mM stock solution of compound 5 was prepared in DMSO and then diluted to a working concentration of 2 mM in culture media (DMEM/Ham's F-12). The compound 5 working stock was diluted again to a final concentration of 50 µM in the culture chamber media, and the cells were incubated for 1 hr. The culture chamber was then gently washed thrice with plain culture media. Cells were fixed with a 1:10 (v/v) solution of formaldehyde fixative (Immunochemistry Technologies, Bloomington, Minn.) and culture media for 5 min, then washed twice with plain culture media. Finally, cells were imaged using a Zeiss Axio Observer inverted microscope (Carl Zeiss Microscopy, Thornwood, N.Y.) equipped with fluorescence detection. Images were acquired using a 10× objective with excitation λ of 450-490 nm (BP 470/40 filter) and emission λ of 500-550 nm (BP 525/50 filter) for detection of compound 5 in A549 cells following 30 sec, 3 min or 10 min exposure to visible light. Also, for localization of the Hoechst dye, a single fluorescence image was acquired at excitation λ at 365 nm; emission λ of 420-470 nm (BP 445/50 filter). Acquired images were universally adjusted to enhance contrast levels (same settings for all acquired images for each detection channel) using Adobe Photoshop CS6 (Adobe, San Jose, Calif.).

2-(4-(diethylamino)phenyl)-3-hydroxy-4H-benzo[g]chromen-4-one (7)

Sodium hydroxide (4.0 mL. 5M, 20 mmol) was added to a suspension of 1-(3-hydroxynaphthalen-2-yl)ethanone (0.931 g, 5 mmol) in ethanol (14 mL) and the resulting mixture was allowed to stir for 30 minutes at room temperature. 4-diethylaminobenzaldehyde (0.886 g, 5 mmol) was added to the mixture and the solution stirred for 24 hours. The reaction mixture was then cooled to 0° C. in an ice bath, hydrogen peroxide (3 mL, 30%) added drop-wise, and the solution was stirred overnight. Acidification of the solution to pH=6.5 with 0.5 M HCl caused the formation of an orange precipitate. The solid was filtered from solution and washed with ethanol (0.754 g, 42% yield). $^1$H NMR (CDCl$_3$, 300 MHz) δ 8.83 (s, 1H), 8.27 (d, J=9.27 Hz, 2H), 8.06 (d, J=8.22 Hz, 1H), 8.02 (s, 1H), 7.93 (d, J=8.22 Hz, 1H), 7.60 (t, J=7.89 Hz, 1H), 7.51 (t, J=7.89 Hz, 1H), 6.9-6.76 (m, 3H), 3.48 (q, J=7.2 Hz, 4H), 1.26 (t, J=7.2 Hz, 6H) ppm. $^{13}$C NMR (CDCl$_3$, 100 MHz) 173.2, 151.7, 149.4, 147.9, 135.8, 135.7, 130.1, 129.6, 128.6, 127.4, 126.2, 125.8, 120.6, 117.6, 114.1, 111.2, 44.7, 12.8 ppm (19 signals expected and observed). FT-IR (KBr, cm$^{-1}$) 3270 ($v_{O-H}$), 1588 ($v_{C=O}$). UV-vis (CH$_3$CN), nm (ε, M$^{-1}$ cm$^{-1}$) 442 (51,000), 301 (22,100). Melting point 191-192° C. Anal. Calc. C$_{23}$H$_{21}$NO$_3$: C, 76.86; H, 5.89; N, 3.90. Found: C, 76.77; H, 5.80; N, 3.96. ESI/APCI-MS, m/z (relative intensity) 360.1594, calc. 360.1594 ([MH]$^+$, 100%).

Synthesis of 8 and 9

Lawsson's Reagent (1.01 g, 2.5 mmol) was added to a solution of 5 or 7 in toluene (120 mL), thoroughly purged with N$_2$, and refluxed for 4 hours producing a dark red solution. The solution was cooled to room temperature, filtered, and the solvent removed under reduced. The residual solid was washed with methanol and hexanes yielding 8 (61% yield) or 9 (60% yield) as dark orange and dark purple solids respectively.

3-Hydroxy-2-phenyl-4H-benzo[g]chromene-4-thione (8)

$^1$H NMR (CDCl$_3$, 300 MHz) δ 9.15 (s, 1H), 8.61 (bs, 1H), 8.49 (d, J=8.1 Hz, 2H), 8.17-8.07 (m, 2H), 7.94 (d, J=8.4 Hz, 1H), 7.70-7.45 (m, 5H) ppm. $^{13}$C NMR (CDCl$_3$, 100 MHz) δ 189.7, 147.5, 145.4, 142.1, 135.8, 131.4, 131.2, 129.8, 129.6, 129.3, 129.1, 129.0, 127.3, 126.7, 126.4, 114.8 ppm (17 signals expected, 16 observed). UV-vis (CH$_3$CN), nm (ε, M$^{-1}$ cm$^{-1}$) 478 (36,700), 456 (29,600), 376 (40,300). Melting Point 151-152° C. Anal. Calc. C$_{19}$H$_{12}$O$_2$S.0.1H$_2$O: C, 74.54; H, 4.02. Found: C, 74.42; H, 4.09. The presence of 0.1 eq H$_2$O was confirmed by integration of the peak at 1.56 ppm in the $^1$H NMR spectrum. ESI/APCI-MS, m/z (relative intensity) 305.0638, calc. 305.0631 ([MH]$^+$, 100%).

2-(4-(diethylamino)phenyl)-3-hydroxy-4H-benzo[g]chromene-4-thione (9)

$^1$H NMR (CDCl$_3$, 300 MHz) δ 9.10 (s, 1H), 8.75 (bs, 1H), 8.46 (d, J=9.0 Hz, 2H), 8.08 (d, J=8.1 Hz, 1H), 8.03 (s, 1H), 7.91 (d, J=8.4 Hz, 1H), 7.57 (t, J=7.5 Hz, 1H), 7.49 (t, J=7.5 Hz, 1H), 6.82 (d, J=9.0 Hz, 2H), 3.49 (q, J=7.2 Hz, 4H), 1.27 (t, J=7.2 Hz, 6H) ppm. $^{13}$C NMR (CDCl$_3$, 100 MHz) 182.6, 150.3, 147.4, 145.0, 134.9, 131.8, 131.0, 129.6, 129.0, 128.3, 127.2, 126.4, 125.9, 116.8, 114.0, 111.5, 44.9, 12.8 ppm (19 signals expected, 18 observed). UV-vis (CH$_3$CN), nm (ε, M$^{-1}$ cm$^{-1}$) 544 (85,800), 400 (19,500), 320 (22,800). Melting point: 176-177° C. Anal. Calc. C$_{23}$H$_{21}$NO$_2$S: C, 73.57; H, 5.64; N, 3.73. Found: C, 73.30; H, 5.79; N, 3.70. ESI/APCI-MS, m/z (relative intensity) 376.1364, calc. 376.1366 ([MH]$^+$, 100%).

Photoreactivity of 7-9.

Identification of 10 and 11. A solution of each molecule (~0.05 mmol) in 5.0 mL CH$_3$CN was placed in a 50 mL round bottom flask under air. The solution was then placed in a Rayonette photoreactor equipped with lamps of appropriate wavelength (7,8: 419 nm lamps; 9: white light lamps with 546 nm cutoff filters) and irradiated until the reaction was determined complete as evidenced by the loss of the lowest energy absorption band (409-544 nm). The solvent was then removed under reduced pressure yielding molecules 10 and 11.

3-((4-(diethylamino)benzoyl)oxy)-2-naphthoic acid (10)

$^1$H NMR (CDCl$_3$, 300 MHz) 8.69 (s, 1H), 8.07 (d, J=9.0 Hz, 2H), 7.96 (d, J=8.4 Hz, 1H); 7.84 (d, J=8.1 Hz, 1H), 7.68 (s, 1H), 7.61 (t, J=8.4 Hz, 1H), 7.53 (t, J=8.1 Hz, 1H), 6.70 (d, J=9.0, 1H), 6.61 (d, J=9.0 Hz, 1H), 3.27 (q, J=6.9 Hz, 4H), 1.31 (t, J=6.9 Hz, 6H) ppm. FT-IR (KBr, cm$^{-1}$) 1716 ($v_{C=O}$). ESI/APCI-MS, m/z (relative intensity) 364.1544, calc. 364.1543 ([MH]$^+$, 100%).

3-(benzoyloxy)naphthalene-2-carbothioic-O-acid (11)

$^1$H NMR (CDCl$_3$, 300 MHz) 8.67 (s, 1H), 8.24 (d, J=7.8 Hz, 2H), 7.99 (d, J=8.7 Hz, 1H), 7.85 (d, J=7.8 Hz, 1H), 7.76 (s, 1H), 7.72-7.39 (m, 5H) ppm. FT-IR (KBr, cm$^{-1}$) 1704 ($v_{C=O}$). ESI/APCI-MS, m/z (relative intensity) 637.0757, calc. 637.0750 ([2M+Na]$^+$, 100%).

3-acetate-2-phenyl-benzo[g]chromen-4-one (12)

A suspension of 3-hydroxy-2-phenyl-benzo[g]chromen-4-one (5, 0.30 g, 1.04 mmol) and acetic anhydride (1.97 mL, 20.81 mmol) in pyridine (5.20 mL) was heated at reflux for 5 hours. The reaction vessel was protected from light. Pre-chilled deionized H$_2$O (18.00 mL) was then added to the warm reaction mixture. The aqueous solution was extracted from dichloromethane (18.00 mL×1). The organic fraction was dried over sodium sulfate, filtered, and the solvent was then removed under reduced pressure to give the residue that was crystallized from dichloromethane and diethyl ether yielding the product as a pale yellow solid (0.33 g, 97%). $^1$H NMR (CDCl$_3$, 300 MHz) δ 8.80 (s, 1H), 8.19-8.16 (m, 2H), 8.15 (s, 1H), 8.06 (s, 1H), 8.03-7.95 (m, 1H), 7.72 (d, J=1.2 Hz, 1H), 7.69 (t, J=1.5 Hz, 1H), 7.67 (d, J=1.5 Hz, 1H), 7.65-7.57 (m, 2H), 2.31 (s, 3H) ppm. $^{13}$C{$^1$H} C NMR (CD$_3$CN, 100 MHz) 173.6, 169.3, 157.9, 152.7, 137.0, 133.1, 132.5, 130.4, 130.1, 129.9, 129.3, 127.5, 127.4, 123.3, 115.7, 20.7 ppm (17 signals expected and 16 observed presumably due to overlap). FTIR (KBr, cm$^{-1}$) 1596 ($v_{C=O}$), 1768 ($v_{C=O}$). UV-vis (CH$_3$CN, nm) (ε, M$^{-1}$ cm$^{-1}$) 363 (4059), 327 (7680), 309 (9350). Melting point 187-189° C. Anal. Calc. C$_{21}$H$_{15}$O$_4$·0.5H$_2$O: C, 74.11; H, 4.74. Found: C, 73.94; H, 4.15. ESI/APCI-MS (relative intensity) calcd. for C$_{21}$H$_{15}$O$_4$ [MH]$^+$: 331.0965. found: 331.0969 (100%).

4-(3-hydroxy-4-oxo-4H-benzo[g]chromen-2-yl)benzoic acid (13)

1-(3-hydroxynaphthalen-2-yl)ethanone (5.33 mmol, 0.9923 g) was combined with NaOH (6 eq. 5M, 6.4 mL) in a 250 mL round bottom flask and allowed to stir at room temperature for 30 minutes. To this solution was added formylbenzoic acid (5.33 mmol, 0.8000 g) and the reaction stirred for 4 hours. It was then cooled to 0° C. in an ice-water bath and H$_2$O$_2$ (6 mL, ca. 30%) was added to the solution drop-wise resulting in the immediate formation of a heavy orange precipitate. The reaction was allowed to stir overnight warming to room temperature, resulting in a dark red solution. Acidification of the solution to pH 6 formed a yellow precipitate. The yellow solid was collected via filtration and washed with several portions of water followed by washing with several portions of ethanol. The solid was removed from the filter and dried in vacuo. Yield 61%. $^1$H NMR (DMSO-d$_6$, 300 MHz) δ 9.55 (bs, 1H), 8.84 (s, 1H), 8.34 (s, 1H), 8.30-8.19 (m, 3H), 8.08 (d, J=7.89, 1H), 8.00 (d, J=7.89, 2H), 7.68 (t, J=6.87, 1H), 7.57 (t, J=6.87, 1H) ppm. FT-IR (KBr, cm$^{-1}$) 3380, 1632, 1584. ESI/APCI, m/z (relative intensity) 333.0765, calc. 333.0758 ([MH]$^+$, 100%).

General Synthetic Procedure for 14-16.

4-(3-hydroxy-4-oxo-4H-benzo[g]chromen-2-yl)benzoic acid (1.20 mmol), 1-ethyl-3-(3 dimethylaminopropyl)carbodiimide hydrochloride (1.44 mmol), hydroxybenzotriazole (1.44 mmol) were combined in DMF (40 mL) and allowed to stir for 2 hours at room temperature with the reaction vessel protected from light. An (6-amino-n-)triphenyl phosphonium bromide (1:1) (1.20 mmol; n=ethyl, hexyl, or octyl)) dissolved in DMF (40 mL) was then added to the reaction mixture. The reaction was allowed to stir for 24 hours at room temperature and then filtered. The DMF was then removed under reduced pressure. The remaining orange-brown solid was dissolved in dichloromethane and washed with deionized H$_2$O. The organic fraction was dried over sodium sulfate, filtered, and the solvent was then removed under reduced pressure resulting in a yellow-brown semi-solid that was washed with ethylacetate and diethyl ether. The solid was dissolved in ethanol and precipitated out in diethyl ether. The obtained solid was dried under reduced pressure yielding the product as brown fine-powdered solid. The n=ethyl compound was further purified using column chromatography. The column was loaded using ethyl acetate, followed by addition of methanol to elute the product, n=ethyl (14): $^1$H NMR (DMSO-d$_6$, 300 MHz) δ 9.07 (bs, 1H), 8.86 (s, 1H), 8.36 (t, J=8.7 Hz, 3H), 8.26 (d, J=8.1 Hz, 1H), 8.08 (d, J=8.1 Hz, 1H), 7.99-7.82 (m, 7H), 7.82-7.65 (m, 6H), 7.58 (t, J=6.9 Hz, 1H), 7.50-7.40 (m, 2H), 7.25-7.11 (m, 4H), 3.98-3.82 (m, 2H), 3.69-3.55 (m, 2H) ppm; $^{31}$P NMR (DMSO-d$_6$, 300 MHz) 21.97 ppm. ESI/APCI-MS, m/z (relative intensity) 620.1999, calc. 620.1985 ([M]$^+$, 100%); n=hexyl (15): $^1$H NMR (MeOH-d$_4$, 300 MHz) δ 8.88 (s, 1H), 8.35 (d, J=5.4 Hz, 2H), 8.08 (t, J=3.6 Hz, 2H), 7.95 (d, J=6.3 Hz, 1H), 7.90-7.70 (m, 15H), 7.67-7.45 (m, 5H), 6.93 (s, 1H), 2.85 (m, 2H), 2.75 (m, 2H), 1.60-1.20 (m, 8H) ppm; $^{31}$P NMR (DMSO-d$_6$, 300 MHz) δ 24.43 ppm; n=octyl (16): $^1$H NMR (MeOH-d$_4$, 300 MHz) δ 7.90-7.70 (m, 15H), 7.67-7.45 (m, 5H), 6.93 (s, 1H), 2.85 (m, 2H), 2.73 (m, 2H), 1.51-1.27 (m, 12H) ppm; $^{31}$P NMR (DMSO-d$_6$, 300 MHz) δ 24.45 ppm.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

REFERENCES

[1] a) S. Garcia-Gallego, G. J. Bernardes, *Angew. Chem. Int. Ed. Engl.* 2014, 53, 9712-9721. b) R. Motterlini, L. E. Otterbein, *Nat. Rev. Drug Discov.* 2010, 9, 728-743.

[2] B. E. Mann, *Top. Organomet. Chem.* 2010, 32, 247-285.

[3] a) M. Chaves-Ferreira, I. S. Albuquerque, D. Matak-Vinkovic, A. C. Coelho, S. M. Carvalho, L. M. Saraiva, C. C. Ramao, G. J. Bernardes, *Angew. Chem. Int. Ed. Engl.* 2015, 54, 1172-1175. b) J. E. Clark, P. Naughton, S. Shurey, C. J. Green, T. R. Johnson, B. E. Mann, R. Foresti, R. Motterlini, *Circ. Res.* 2003, 93, e2-e8.

[4] PhotoCORMs: a) U. Schatzschneider, *Br. J. Pharmacol.* 2014, doi: 10.1111/bph.12688. b) M. A. Gonzalez, P. K.

Mascharak, *J. Inorg. Biochem.* 2014, 133, 127-135. c) I. Chakraborty, S. J. Carrington, P. K. Mascharak, *Acc. Chem. Res.* 2014, 47, 2603-2611. d) F. Zobi, *Future Med. Chem.* 2013, 2, 175-188.

[5] Esterase and phosphatase-triggered CO release: S. Romanski, B. Kraus, U. Schatzschneider, J-M. Neudoerfl, S. Amslinger, H. G. Schamlz, *Angew. Chem. Int. Ed. Engl.* 2011, 50, 2392-2396.

[6] a) S. J. Carrington, I. Chakraborty, P. K. Mascharak, *Chem. Commun.* 2013, 49, 11254-11256. b) C. S. Jackson, S. Schmitt, Q. P. Dou, J. J. Kodanko, *Inorg. Chem.* 2011, 50, 5336-5338.

[7] a) M. N. De Mantos, C. C. Ramao, US Patent 2007219120A1, 2007. b) S. D. Friis, R. H. Taaning, A. T. Lindhardt, T. Skrydstrup, *J. Am. Chem. Soc.* 2011, 133, 18114-18117. c) R. Motterlini, P. Sawle, J. Hammad, S. Bains, R. Alberto, R. Foresti, C. J. Green, *FASEB J.* 2005, 19, 284-286. d) T. S. Pitchumony, B. Spingler, R. Motterlini, R. Alberto, *Org. Biomol. Chem.* 2010, 8, 4849-4854.

[8] a) L. A. P. Antony, T. Slanina, P. Sebej, T. Solomek, P. Klan, *Org. Lett.* 2013, 15, 4552-4555. b) P. Peng, C. Wang, Z. Zhi, V. K. Johns, L. Ma, J. Oyer, A. Copik, R. Igarashi, Y. Liao, *Org. Biomol. Chem.* 2013, 11, 6671-6674. c) D. Wang, E. Viennois, K. Ji, K. Damera, A. Draganov, Y. Zheng, C. Dai, D. Merlin, and B. Wang, *Chem. Commun.* 2014, 50, 15890-14893. d) E. Palao, T. Slanina, L. Muchova, T. Solomek, L. Vitek, P. Klan, *J. Am. Chem. Soc.* 2016, 138 126-133.

[9] C. C. Romao, W. A. Blattler, J. D. Seixas and G. J. L. Bernardes, *Chem. Soc. Rev.* 2012, 41, 3571-3583.

[10] a) B. Ramano, E. Pagano, V. Montanaro, A. L. Fortunato, N. Millie, F. Borrelli, *Phytother. Res.* 2013, 27, 1588-1596. b) F. Perez-Vizcaino, J. Duarte, *Mol. Aspects. Med.* 2010, 31, 478-494.

[11] S. Fetzner, *Appl. Environ. Microbiol.* 2012, 78, 2505-2514.

[12] a) R. Sokolova, S. Ramesova, H. Degano, M. Hromadova, M. Gal, J. Zabka, *Chem. Commun.* 2012, 48, 3433-3435. b) I. G. Zenkevich, A. Y. Eshchenko, S. V. Makarova, A. G. Vitenberg, Y. G. Dobryakov, V. A. Utsal, *Molecules* 2007, 12, 654-672.

[13] S. L. Studer, W. E. Brewer, M. L. Martinez, P-T. Chou, *J. Am. Chem. Soc.* 1989, 111, 7643-7644.

[14] a) T. Matsuura, T. Takemoto, R. Nakashima, *Tetrahedron* 1973, 29, 3337-3340. b) T. Matsuura, T. Takemoto, R. Nakashima, *Tetrahedron* 1971, 12, 1539-1540.

[15] a) J. Algar, J. P. Flynn, *Proc. Roy. Irish Acad.* 1934, 42B, 1. b) B. Oyamada, *Bull. Chem. Soc. Jpn.* 1935, 10, 182-186.

[16] CCDC 1025106 contains the supplementary crystallographic data for this paper. These data may be obtained free of charge from the Cambridge Crystallographic Data Centre via www.ccdc.cam.ac.uk/data_request/cif.

[17] a) M. C. Etter, Z. Urbanczyk-Lipowska, S. Baer, P. F. Barbara, *J. Mol. Struct.* 1986, 144, 155-167. b) K. Hino, K. Nakajima, M. Kawahara, I. Kiyota, H. Sekiya, *Bull. Chem. Soc. Jpn.* 2011, 84, 1234-1236.

[18] H-R. Park, Y. Duan, J-K. Park, K-M. Bark, *Bull. Korean Chem. Soc.* 2013, 34, 211-220.

[19] B. Dick, N. P. Ernsting, *J. Phys. Chem.* 1987, 91, 4261-4265.

[20] http://www.molinspiration.com/services/logp.html

[21] P. Ertl, B. Rohde, and P. Selzer, *J. Med. Chem.* 2000, 43, 3714-3717.

[22] pKa calculated to be 9.5 using http://epoch.uky.edu/ace/public/pKa.jsp.

[23] L. K. Wareham, R. K. Poole, M. Tinajero-Trejo *J. Biol. Chem.* 2015, 290, 18999-19007.

[24] K. Yamasaki, V. T. Chuang, T. Maruyama, M. Otagiri, *Biochim. Biophys. Acta* 2013, 1830, 5435-5443.

[25] S. Naveenraj, S. J. Anandan, *Photochem. Photobiol. C* 2013, 14, 53-71.

[26] D. Agudelo, P. Bourassa, J. Bruneau, G. Berube, E. Asselin, H. Tajmir-Riahi, *PLoS One.* 2012, 7, e43814.

[27] O. Trott, A. J. Olson, *J. Comput. Chem.* 2010, 31, 455-461.

[28] S. Pal, C. Saha, M. Hossain, S. K. Dey, G. S. Kumar, *PLoS One.* 2012, 7, e43321.

[29] a) V. V. Shynkar, A. S. Klymchenko, C. Kunzelmann, G. Duportail, C. D. Muller, A. P. Demchenko, J-M. Freyssinet, Y. Mely, *J. Am. Chem. Soc.* 2007, 129, 2187-2193. b) G. Duportail, A. Klymchenko, Y. Mely, A. Demchenko, *FEBS Lett.* 2001, 508, 196-200. c) O. P. Bondar, V. G. Pivovarenko, E. S. Rowe, *Biochim Biophys. Acta Biomembranes* 1998, 1369, 119-130. d) A. Sytnik, D. Gormin, M. Kasha, *Proc. Natl. Acad. Sci. USA* 1994, 91, 11968-11972.

[30] a) A. L. Macanita, F. Elisei, G. G. Aloisi, F. Ortica, V. Boninfacio, A. Dias, E. Leitao, M. J. Caldeira, C. D. Maycock, R. S. Becker, *Photochem. Photobiol.* 2003, 77, 22-29. b) M. Borges, A. Ramao, O. Matos, C. Marzano, S. Caffieri, R. S. Becker A. L. Macanita, *Photochem. Photobiol.* 2002, 75, 97-106. c) F. Elisei, J. C. Lima, F. Ortica, G. Aloisi, M. Costa, E. Leitao, I. Abreu, A. Dias, V. Bonifacio, J. Medeiros, A. L. Macanita, R. S. Becker, *J. Phys. Chem. A* 2000, 104, 6095-6102.

[31] G. D'Andrea, *Fitoterapia* 2015, 106, 256-271.

[32] C. Perez, K. B. Daniel, S. M. Cohen, *ChemMedChem* 2013, 8, 16624667.

[33] a) N. Schallner, L. E. Otterbein, *Frontiers in Physiology* 2015, 6, doi: 10.3389/fphys.2015.00017. b) A. S. Almeida, C. Figueiredo-Pereira, H. L. A. Vieira, *Frontiers in Physiology* 2015, 6, doi: 10.3389/fphys.2015.00033.

[34] R. A. J. Smith, R. C. Hartley, M. P. Murphy, *Antioxid. Redox Signal* 2011, 15, 3021-3038.

[35] W. L. F. Armarego and D. D. Perrin, *Purification of Laboratory Chemicals,* 4th ed.; Betterworth-Heinemann: Boston, Mass. (1996).

[36] a) C. G. Hatchard, C. A. Parker, *Proc. R. Soc. London A* 1956, 235, 518-536. b) H. J. Kuhn, S. E. Braslaysky, R. Schmidt, *Pure Appl. Chem.* 2004, 76, 2105-2146.

[37] K. Grubel, S. L. Saraf, S. N. Anderson, B. J. Laughlin, R. C. Smith, A. M. Arif, L. M. Berreau, *Inorg. Chim. Acta* 2013, 407, 91-97.

[38] a) M. P. O'Farrell, D. M. S. Wheeler, M. M. Wheeler, T. S. Wheeler, *J. Chem. Soc.* 1955, 3986-3992. b) G. Razniewska-Lazecka, A. Dambska, A. Janowski, A. *Mag. Reson. Chem.* 1986, 24, 365-367.

[39] L. E. Shorey, A. M. Hagman, D. E. Williams, E. Ho, R. H. Dashwood, A. D. Benninghoff, *PLoS One* 2012, 7, e34975.

[40] S. L. Saraf, T. J. Fish, A. D. Benninghoff, A. A. Buelt, R. C. Smith, L. M. Berreau, *Organometallics* 2014, 33, 6341-6351.

What is claimed is:

1. A compound, or salt thereof, comprising the formula:

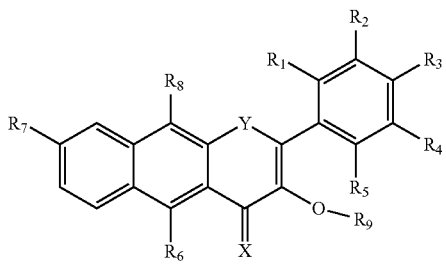

wherein:
Y is a member selected from the group consisting of O or S;
X is a member selected from the group consisting of O or S;
$R_1$, $R_2$, $R_4$, $R_5$, $R_6$, $R_7$, $R_8$ are each a member selected from the group consisting of —H, —COOH, —CSOH, —COOR', —CONH$_2$, —CONHR', CON(R')$_2$, —COR', —F, —Cl, —Br, —I, —CN, —NO$_2$, —OH, —OR', —SH, —SR', —O—CO—R', —NH$_2$, —NHR', —NR$_2$', —NH(R')$_2$, —NH—CO—R', —NR'—CO—R', —SO$_3$R', —OSO$_2$R', —C$_{5\text{-}15}$ aryl, —C$_{1\text{-}12}$alkyl, —C$_{2\text{-}12}$ alkenyl, C$_{2\text{-}12}$ alkynyl, C$_{1\text{-}12}$ alkyl-C$_{5\text{-}15}$ aryl, C$_{2\text{-}12}$ alkenyl-C$_{5\text{-}15}$ aryl, an amino acid, an aminoglycoside, a carbohydrate, and a heterocycle containing O, N, or S;
wherein the —C$_{5\text{-}15}$ aryl is optionally substituted with —COOH, —CSOH, —COOR', —CONH$_2$, —CONHR', CON(R')$_2$, —COR', —F, —Cl, —Br, —I, —CN, —NO$_2$, —OH, —OR', —SH, —SR', —O—CO—R', —NH$_2$, —NHR', —NR$_2$', —NH(R'), —NH—CO—R', —NR'—CO—R', —SO$_3$R', or —OSO$_2$R';
wherein the —C$_{1\text{-}12}$ alkyl, the —C$_{2\text{-}12}$ alkenyl, the C$_{2\text{-}12}$ alkynyl, the C$_{1\text{-}12}$ alkyl-C$_{5\text{-}15}$ aryl, the C$_{2\text{-}12}$ alkenyl-C$_{5\text{-}15}$ aryl, or the heterocycle is optionally substituted with —COOH, —CSOH, —COOR', —CONH$_2$, —CONHR', CON(R')$_2$, —COR', —F, —Cl, —Br, —I, —CN, —NO$_2$, —OH, —OR', —SH, —SR', —O—CO—R', —NH$_2$, —NHR', —NR$_2$', —NH(R')$_2$, —NH—CO—R', —NR'—CO—R', —SO$_3$R', —OSO$_2$R', —P(aryl)$_3$, P(alkyl)$_3$, or PO$_3^2$, or HPO$_3$;
wherein R' is a member selected from the group consisting of C$_{5\text{-}15}$ aryl, —C$_{1\text{-}12}$ alkyl, and —C$_{2\text{-}12}$ alkenyl; and
$R_3$ is a member selected from the group consisting of —H, —COOH, —CSOH, —COOR", —CONH$_2$, —CONHR", CON(R")$_2$, —COR", —F, —Cl, —Br, —I, —CN, —NO$_2$, —OH, —OR", —SH, —SR", —O—CO—R", —NH$_2$, —NHR", —NR$_2$", —NH(R")$_2$, —NH—CO—R", —NR"—CO—R", —SO$_3$R", —OSO$_2$R", —P(aryl)$_3$, P(alkyl)$_3$, PO$_3^2$, HPO$_3$, C$_{5\text{-}15}$ aryl, C$_{1\text{-}12}$ alkyl, —C$_{2\text{-}12}$ alkenyl, C$_{2\text{-}12}$ alkynyl, C$_{1\text{-}12}$ alkyl-C$_{5\text{-}15}$ aryl, C$_{2\text{-}12}$ alkenyl-C$_{5\text{-}15}$ aryl, amino acids, aminoglycosides, carbohydrates, or heterocycles containing O, N, or S;
wherein the C$_{5\text{-}15}$ aryl, the C$_{1\text{-}12}$ alkyl, the —C$_{2\text{-}12}$ alkenyl, the C$_{2\text{-}12}$ alkynyl, the C$_{1\text{-}12}$ alkyl-C$_{5\text{-}15}$ aryl, the C$_{2\text{-}12}$ alkenyl-C$_{5\text{-}15}$ aryl, or the heterocycle is optionally substituted with —COOH, —CSOH, —COOR", —CONH$_2$, —CONHR", CON(R")$_2$, —COR", —F, —Cl, —Br, —I, —CN, —NO$_2$, —OH, —OR", —SH, —SR", —O—CO—R", —NH$_2$, —NHR", —NR$_2$', —NH(R")$_2$, —NH—CO—R", —NR"—CO—R", —SO$_3$R", —OSO$_2$R", —P(aryl)$_3$, P(alkyl)$_3$, PO$_3^2$, or HPO$_3$;
wherein R" is a member selected from the group consisting of C$_{5\text{-}15}$ aryl, —C$_{1\text{-}12}$ alkyl, —C$_{2\text{-}12}$ alkenyl, and C$_{2\text{-}12}$ alkynyl, each of which is optionally unsubstituted or substituted with phosphonium; and
$R_9$ is —H or —COR"",
wherein R"" is a member selected from the group consisting of C$_{5\text{-}15}$ aryl, —C$_{1\text{-}12}$ alkyl, —C$_{2\text{-}12}$ alkenyl, and C$_{2\text{-}12}$ alkynyl.

2. The compound of claim 1, wherein $R_1$, $R_2$, $R_4$, $R_5$, $R_6$, $R_7$, $R_8$, $R_9$ are the same.

3. The compound of claim 1, wherein the compound is:

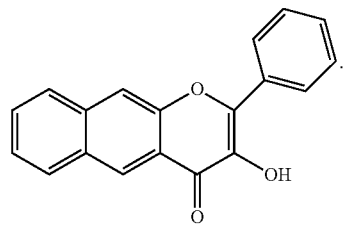 [SMILES: O=c1c(O)c(-c2ccccc2)oc2cc3ccccc3cc12]

4. The compound of claim 1, wherein the compound is:

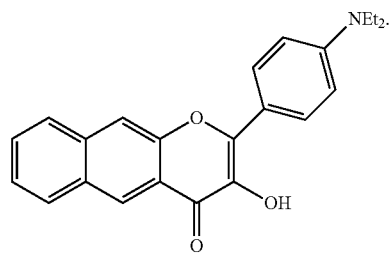

5. The compound of claim 1, wherein the compound is:

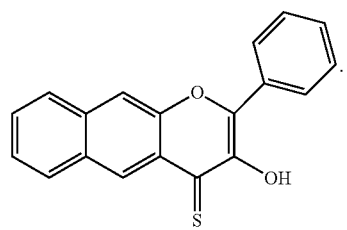 [SMILES: Oc1c(-c2ccccc2)oc2cc3ccccc3cc2c1=S]

6. The compound of claim 1, wherein the compound is:

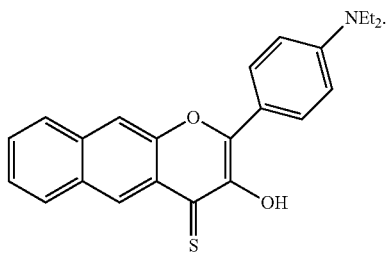

7. The compound of claim 1, wherein the compound is:

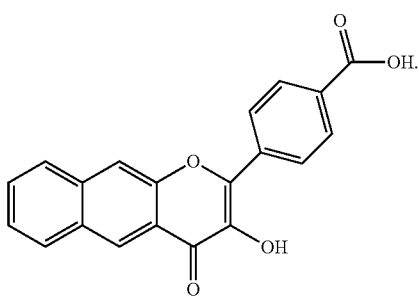 [SMILES: O=C(O)c1ccc(-c2oc3cc4ccccc4cc3c(=O)c2O)cc1]

8. The compound of claim 1, wherein the compound is:

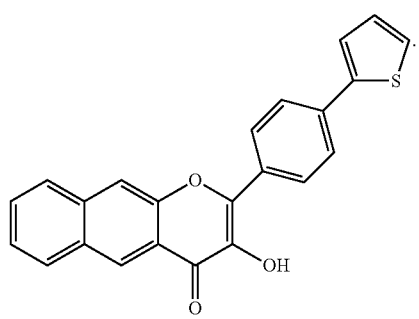 [SMILES: O=c1c(O)c(-c2ccc(-c3cccs3)cc2)oc2cc3ccccc3cc12]

9. The compound of claim 1, wherein the compound is:

10. The compound of claim 1, wherein the compound is:

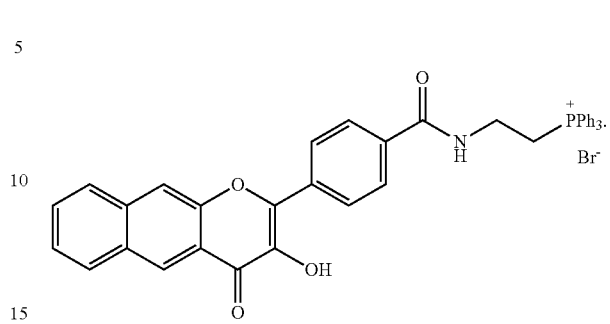

11. The compound of claim 1, wherein the compound is:

12. The compound of claim 1, wherein the compound is:

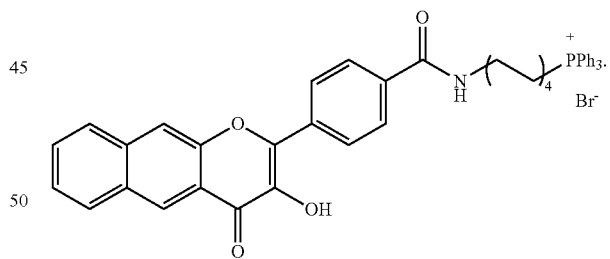

13. A composition, comprising the compound of claim 1.

14. The composition of claim 13, further comprising a pharmaceutically acceptable carrier.

* * * * *